(12) United States Patent
Faust et al.

(10) Patent No.: US 7,786,217 B2
(45) Date of Patent: Aug. 31, 2010

(54) ORGANOMETALLIC-POLYISOMONOOLEFIN BLOCK COPOLYMERS

(75) Inventors: Rudolf Faust, Lexington, MA (US);
Tomoya Higashihara, Tewksbury, MA (US)

(73) Assignee: University of Massachusetts Lowell, Lowell, MA (US)

( * ) Notice: Subject to any disclaimer, the term of this patent is extended or adjusted under 35 U.S.C. 154(b) by 16 days.

(21) Appl. No.: 11/734,230

(22) Filed: Apr. 11, 2007

(65) Prior Publication Data

US 2008/0255330 A1 Oct. 16, 2008

(51) Int. Cl.
*C08F 30/04* (2006.01)
(52) U.S. Cl. ............... 525/201; 525/326.6; 525/333.7; 526/241
(58) Field of Classification Search ......... 526/173, 526/240, 241, 88, 89; 525/201, 326.6, 333.7; 430/270.1
See application file for complete search history.

(56) References Cited

U.S. PATENT DOCUMENTS

| 5,212,248 | A  | * | 5/1993 | Knoll et al. ............ 525/245 |
| 7,105,611 | B2 | * | 9/2006 | Kimura et al. .......... 525/314 |
| 2006/0013867 | A1 | * | 1/2006 | Richard et al. ......... 424/449 |
| 2006/0264577 | A1 | * | 11/2006 | Faust et al. ........... 525/242 |
| 2008/0051542 | A1 | * | 2/2008 | Strickler ............. 526/273 |

FOREIGN PATENT DOCUMENTS

WO    WO 2007117566 A2   *   10/2007

OTHER PUBLICATIONS

Gulimov (Copolymerization of alpha-cyclopentadienylideneethylferrocene with isobutylene, butadiene, and isoprene. Izvestiya Vysshikh Uchebnykh Zavedenii, Khimiya I Khimicheskaya Technologiya. 1988, 31(6), pp. 136-138).*
CAPlus AN 1989:25192, AN 1982:617664 and RN 79622-55-2, 3 pages total.*
Abd-El-Aziz, Alaa S. et al., "Macromolecules Containing Metal and Metal-like Elements," vol. 3, Biomedical Applications, Wiley-Interscience (2004).
Durkee, David A. et al., "Catalysts from Self-Assembled Organometallic Block Copolymers," *Adv. Mater.*, vol. 17:2003-2006 (2005).
Higashihara, Tomoya et al., "New block copolymers comprised of polyisobutylene and poly(vinylferrocene) segments," American Chemical Society, The 233rd ACS National Meeting, Chicago, IL (2007).

(Continued)

*Primary Examiner*—Milton I Cano
*Assistant Examiner*—Brieann R Fink
(74) *Attorney, Agent, or Firm*—McCarter & English, LLP

(57) ABSTRACT

The present invention provides copolymers which include a plurality of constitutional units that correspond to at least one cationically polymerizable isomonoolefin species and a plurality of constitutional units that correspond to at least one anionically polymerizable monomer species selected from the group consisting of monomers of formula (I):

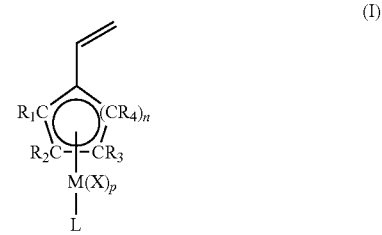

(I)

wherein $R_1$, $R_2$, $R_3$, $R_4$, n, p, M, X, and L are defined herein. The present invention also provides methods for making and using (e.g., in articles of manufacture such as medical devices) the copolymers of the present invention.

22 Claims, 10 Drawing Sheets

OTHER PUBLICATIONS

Higashihara, Tomoya et al., "New block copolymers comprised of polyisobutylene and poly(vinylferrocene) segments," *Polymer Preprints*, vol. 48(1):836-837 (2007).

Higashihara, Tomoya et al., "Synthesis of Novel Block Copolymers Comprised of Polyisobutylene and Poly(vinylferrocene) Segments," *Macromolecules*, vol. 40:7453-7463 (2007).

Nuyken, Oskar et al., "Anionic homo- and block copolymerization of vinyl-ferrocene," *Macromol. Chem. Phys.*, vol. 198:3353-3363 (1997).

Peckham, Timothy J. et al., "Living Anionic Polymerization of Phosphorus-Bridged [1]Ferrocenophanes: Synthesis and Characterization of Well-Defined Poly(ferrocenylphosphine) Homopolymers and Block Copolymers," *Macromolecules*, vol. 32:2830-2837 (1999).

Rulkens, Ron et al., "Anionic Ring-Opening Oligomerization and Polymerization of Silicon-Bridged [1]Ferrocenophanes: Characterization of Short-Chain Models for Poly(ferrocenylsilane) High Polymers," *J. Am. Chem. Soc.*, vol. 116:797-798 (1994).

Temple, Karen et al., "Living Anionic Ring-Opening Polymerization of Unsymmetrically Substituted Silicon-Bridged [1]Ferrocenophanes; A Route to Organometallic Block Copolymers with Amorphous Poly(ferrocenylsilane) Blocks," *Journal of Inorganic and Organometallic Polymers*, vol. 9(4):189-198 (1999).

International Search Report for Application No. PCT/US2008/004787, dated Jul. 14, 2008.

\* cited by examiner

PIB-AllylX (X = Cl, Br, and I)

PVFeLi

**PIB-*b*-PVFe**

ORGANOMETALLIC-POLYISOMONOOLEFIN BLOCK COPOLYMERS

FIELD OF THE INVENTION

This invention relates to block copolymers which include at least one polyisomonoolefin and at least one organometallic polymer, as well as processes for the preparation of such copolymers.

BACKGROUND OF THE INVENTION

Copolymers have numerous commercial applications, for instance, unique properties in pure form, blends, melts, solutions, etc. These properties lead to the use of copolymers in a wide range of products, for example, compatiblilizers, adhesives and dispersants. An advantage of combining various polymerization techniques (e.g., cationic and anionic polymerization techniques) is that new copolymers, each with its own unique properties, can be prepared which could not otherwise be prepared using a single polymerization method.

Polyisoolefins are prepared by cationic polymerization, and described, for example, in Müller et al., who reported that poly(alkyl methacrylate)-b-polyisobutylene and poly(alkyl methacrylate)-b-polyisobutylene-b-poly(alkyl methacrylate) copolymers can be prepared by the combination of cationic and anionic polymerization techniques. See Feldthusen, J. et al. *Macromolecules,* 1997, 30, 6989-6993; Feldthusen, J. et al. *Macromolecules* 1998, 31, 578-585.

Polymer-ferrocene conjugates have been described, e.g., Neuse, E. W.; *Macromolecules Containing Meal and Metal-Like Elements, Vol. 3: Biomedical Applications*; Abd-El-Aziz, A. S. et al. Eds.; John Wiley & Sons, 2004. Additionally, examples of main chain iron containing block copolymers such as poly(ferrocenylsilane), and poly(ferrocenylphosphine) exist (See., e.g., (a) Rulkens, R. et al. *J. Am. Chem. Soc.* 1994, 116, 797-8. (b) Temple, K. et al. *J. Inorg. Organomet. Polym.* 1999, 9, 189-98. and (c) Peckman, T. J. et al. *Macromolecules* 1999, 32, 2830-7.), however, relatively few examples of side chain iron containing block copolymers have been reported.

SUMMARY OF THE INVENTION

Since the discovery of the living anionic polymerization of vinylferrocene (VFe) in the 1990's, block copolymers comprised of poly(vinylferrocene) and poly(methyl methacrylate), polystyrene and polyisoprene have been prepared. See, e.g., (a) Nuyken, I. et al. *Macromol. Chem. Phys.* 1997, 198, 3353-63 and (b) Durkee, D. A. et al. *Adv. Mater.* 2005, 17, 2003-6. Until now, however, no block copolymers that include poly(vinylferrocene) and polyisomonoolefin, e.g., polyisobutylene, have been successfully prepared.

The present invention provides novel copolymers which combine the beneficial properties of the metal containing polymers with those of the polyisomonoolefin polymers. Polyisomonoolefins are employed because the polymer chain is fully saturated and thus the thermal and oxidative stability of this polymer are typically very good. Such polyisoolefins may be included in block copolymers. Additionally, metal-containing polymers, e.g., poly(vinylferrocene) are employed because of their beneficial properties, e.g., thermal stability (400° C.), high $T_g$ (190° C.~220° C.), high ultraviolet and γ-radiation absorbability, inertness to air, semi-conductivity (e.g., after doping), and/or redox activity. Additionally, polymer-ferrocene conjugates exhibit high antiproliferative activity and low in vivo toxicity. The resulting copolymers have a number of advantages, including, e.g., their modifiable elastomeric properties.

Accordingly, in one aspect the present invention is directed to a copolymer that includes (a) a plurality of constitutional units that correspond to at least one cationically polymerizable isomonoolefin species and (b) a plurality of constitutional units that correspond to at least one anionically polymerizable monomer species. The anionically polymerizable monomer species include monomers of formula (I):

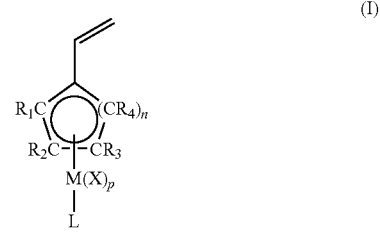

wherein
  $R_1$, $R_2$, $R_3$ and each occurrence of $R_4$ are each independently selected from the group consisting of hydrogen, $C_1$-$C_{20}$ alkyl, $C_1$-$C_{20}$ alkyl substituted with $C_1$-$C_{20}$ aryl, $C_1$-$C_{20}$ aryl, halogen, $C_1$-$C_{20}$ haloalkyl, hydroxyl, $C_1$-$C_{20}$ alkoxy, amino, $C_1$-$C_{20}$ alkylamino, di($C_1$-$C_{20}$ alkyl)amino, thiol, $C_1$-$C_{20}$ alkylthio, carboxylate, $C_1$-$C_{20}$ acyl, nitro, cyano, or at least two R groups are taken together to form a fused ring structure;
  n is an integer of 1 or 2;
  p is an integer of 0 or 1;
  M is a metal;
  X is a counterion; and
  L is one or more ancillary ligands.

In some embodiments, n is 1. In some embodiments, M is, for example, Fe, Co, Ni, Ru, Ti, Zr or Os.

In some embodiments, L is a ligand of formula (II):

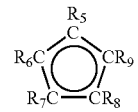

wherein $R_5$, $R_6$, $R_7$, $R_8$ and $R_9$ are each independently selected from the group consisting of hydrogen, $C_1$-$C_{20}$ alkyl, $C_1$-$C_{20}$ alkyl substituted with $C_1$-$C_{20}$ aryl, $C_1$-$C_{20}$ aryl, halogen, $C_1$-$C_{20}$ haloalkyl, hydroxyl, $C_1$-$C_{20}$ alkoxy, amino, $C_1$-$C_{20}$ alkylamino, di($C_1$-$C_{20}$ alkyl) amino, thiol, $C_1$-$C_{20}$ alkylthio, carboxylate, $C_1$-$C_{20}$ acyl, nitro, cyano, or at least two R groups are taken together to form a fused ring structure.

In some embodiments, the monomer of formula (I) includes, but is not limited to, vinylferrocene, vinylcobaltocene, vinylnickelocene, vinylruthenocene, vinyltitanocene, vinylzirconocene, and vinylosmocene.

In some embodiments, the cationically polymerizable isomonoolefin species includes, but is not limited to, isobutylene, 2-methylbutene, 3-methyl-1-butene, 4-methyl-1-pentene and beta-pinene.

In some embodiments, the number average molecular weight of the copolymer ranges from about 10,000 to about 1,000,000.

In some embodiments, the plurality of constitutional units that correspond to at least one cationically polymerizable isomonoolefin species includes a plurality of constitutional units that correspond to a single cationically polymerizable isomonoolefin species. In some embodiments, the cationically polymerizable isomonoolefin species includes isobutylene.

In some embodiments, the plurality of constitutional units that correspond to at least one anionically polymerizable monomer species includes a plurality of constitutional units that correspond to a single anionically polymerizable monomer species. In some embodiments, the anionically polymerizable monomer species includes vinylferrocene.

In some embodiments, the copolymer is a linear copolymer. In other embodiments, the copolymer is a branched copolymer.

In some aspects, the present invention provides methods for making the copolymers described herein. The method typically includes:

contacting an end functionalized polyisomonoolefin with a living organometallic polymer in the presence of an initiator, wherein the living organometallic polymer includes a plurality of constitutional units that correspond to at least one anionically polymerizable monomer species selected from the group consisting of monomers of formula (I):

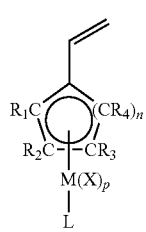

wherein
$R_1$, $R_2$, $R_3$ and each occurrence of $R_4$ are each independently selected from the group consisting of hydrogen, $C_1$-$C_{20}$ alkyl, $C_1$-$C_{20}$ alkyl substituted with $C_1$-$C_{20}$ aryl, $C_1$-$C_{20}$ aryl, halogen, $C_1$-$C_{20}$ haloalkyl, hydroxyl, $C_1$-$C_{20}$ alkoxy, amino, $C_1$-$C_{20}$ alkylamino, di($C_1$-$C_{20}$ alkyl)amino, thiol, $C_1$-$C_{20}$ alkylthio, carboxylate, $C_1$-$C_{20}$ acyl, nitro, cyano, or at least two R groups are taken together to form a fused ring structure;
n is an integer of 1 or 2;
p is an integer of 0 or 1;
M is a metal;
X is a counterion; and
L is one or more ancillary ligands.

In some embodiments, the monomer of formula (I) includes, but is not limited to, vinylferrocene, vinylcobaltocene, vinylnickelocene, vinylruthenocene, vinyltitanocene, vinylzirconocene, and vinylosmocene.

In some embodiments, the end functionalized polyisomonoolefin is an allyl-halide end functionalized polyisomonoolefin.

In some embodiments, the end functionalized polyisomonoolefin is a silyl end functionalized polyisomonoolefin.

In some embodiments, the polyisomonoolefin is polyisobutylene.

In some embodiments, the initiator includes, but is not limited to, methyllithium, ethyllithium, isopropyllithium, n-butyllithium, sec-butyllithium, tert-butyllithium, tert-octyllithium, phenyllithium, 1-naphthyllithium, p-tolyllithium, cyclohexyllithium and/or 4-cyclohexylbutyllithium.

In some aspects, the present invention provides an article of manufacture that includes at least one copolymer described herein. In some embodiments, the article of manufacture is an insertable or implantable medical device, e.g., a catheter, an endotracheal tube, a tracheostomy tube, a wound drainage device, a wound dressing, a stent, an implant, an intravenous catheter, a medical adhesive, a suture, a shunt, a gastrostomy tube, medical tubing, a cardiovascular product, a heart valve, a pacemaker lead, a guidewire and a urine collection device.

DETAILED DESCRIPTION

Figure 1:
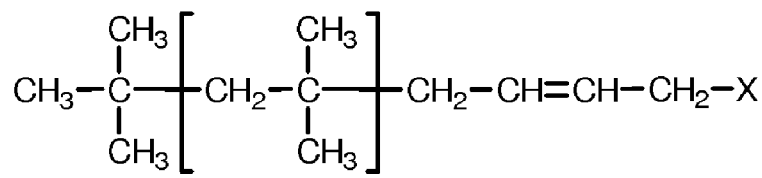
FIG. 1 is a scheme of the synthesis of an exemplary copolymer of the invention, PIB-b-PVFe, by the coupling reaction of PIB-AllylX with PVFeLi.
Figure 1:
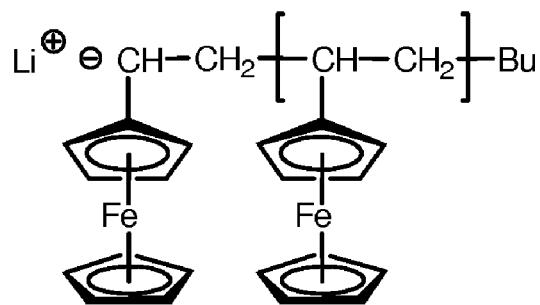
Figure 1:
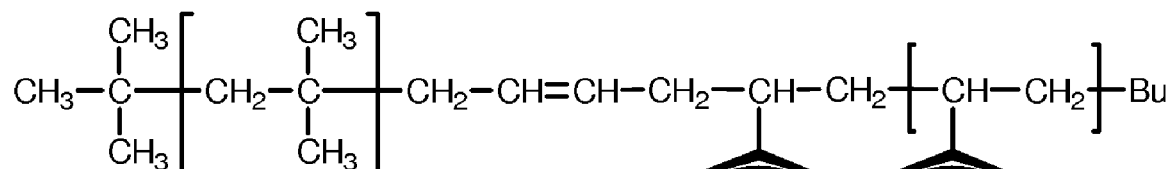
Figure 1:
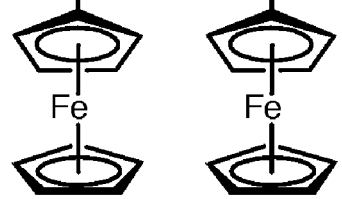

The present invention is based, at least in part, on the discovery of novel copolymers which include a plurality of constitutional units that correspond to at least one cationically polymerizable olefin species and a plurality of constitutional units that correspond to at least one anionically polymerizable monomer species selected from the metal-containing monomers described herein. Such copolymers exhibit advantageous properties, e.g., modifiable elastomeric properties, which are dependent upon the monomers utilized.

Definitions

In order to more clearly and concisely describe the subject matter of the claims, the following definitions are intended to provide guidance as to the meaning of specific terms used herein.

It is to be noted that the singular forms "a," "an," and "the" as used herein include "at least one" and "one or more" unless stated otherwise. Thus, for example, reference to "a pharmacologically acceptable carrier" includes mixtures of two or more carriers as well as a single carrier, and the like.

Numerous values and ranges are recited in connection with various embodiments of the present invention, e.g., number of constitutional units present in a block. It is to be understood that all values and ranges which fall between the values and ranges listed are intended to be encompassed by the present invention unless explicitly stated otherwise. Additionally, it is also to be understood that all numerical values listed herein are implicitly modified by the term "about" unless specifically stated otherwise.

As used herein, the term "polymer" refers to a molecule that contains one or more chains, each containing multiple copies of one or more constitutional units. An example of a common polymer is polystyrene

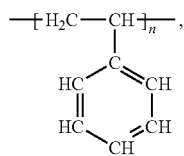

where n is an integer, typically an integer of 10 or more, more typically on the order of 10's, 100's, 1000's or even more, in which the constitutional units in the chain correspond to styrene monomers:

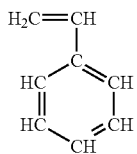

(i.e., they originate from, or have the appearance of originating from, the polymerization of styrene monomers—in this case the addition polymerization of styrene monomers). Copolymers are polymers that contain at least two dissimilar constitutional units.

As used herein a polymer "block" refers to a grouping of 10 or more constitutional units, commonly 20 or more, 50 or more, 100 or more, 200 or more, 500 or more, or even 1000 or more units, and can be branched or unbranched. A "chain" is a linear (unbranched) grouping of 10 or more constitutional units (i.e., a linear block). In the present invention, the constitutional units within the blocks and chains are not necessarily identical, but are related to one another by the fact that that they are formed in a common polymerization technique, e.g., a cationic polymerization technique or anionic polymerization technique.

As used herein, "alkyl" groups include saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (isopropyl, tert-butyl, sec-butyl, isobutyl, etc.), and alkyl-substituted alkyl groups (e.g., alkyl-substituted cycloalkyl groups and cycloalkyl-substituted alkyl groups). In certain embodiments, a straight-chain or branched-chain alkyl group may have 30 or fewer carbon atoms in its backbone, e.g., $C_1$-$C_{30}$ for straight-chain or $C_3$-$C_{30}$ for branched-chain. In certain embodiments, a straight-chain or branched-chain alkyl group may have 20 or fewer carbon atoms in its backbone, e.g., $C_1$-$C_{20}$ for straight-chain or $C_3$-$C_{20}$ for branched-chain, and more preferably 18 or fewer. Likewise, preferred cycloalkyl groups have from 4-10 carbon atoms in their ring structure, and more preferably have 4-7 carbon atoms in the ring structure. The term "lower alkyl" refers to alkyl groups having from 1 to 6 carbons in the chain, and to cycloalkyl groups having from 3 to 6 carbons in the ring structure. The term "$C_1$-$C_6$" as in "$C_1$-$C_6$ alkyl" means alkyl groups containing 1 to 6 carbon atoms.

Moreover, unless otherwise specified the term alkyl includes both "unsubstituted alkyls" and "substituted alkyls," the latter of which refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclic, alkylaryl, or aromatic (including heteroaromatic) groups.

The term "heterocyclic group" includes closed ring structures analogous to carbocyclic groups in which one or more of the carbon atoms in the ring is an element other than carbon, for example, nitrogen, sulfur, or oxygen. Heterocyclic groups may be saturated or unsaturated. Additionally, heterocyclic groups (such as pyrrolyl, pyridyl, isoquinolyl, quinolyl, purinyl, and furyl) may have aromatic character, in which case they may be referred to as "heteroaryl" or "heteroaromatic" groups.

The terms "aromatic group" and "aryl group" are used interchangeably to include unsaturated and aromatic cyclic hydrocarbons as well as unsaturated and aromatic heterocycles containing one or more rings. Aryl groups may also be fused or bridged with alicyclic or heterocyclic rings that are not aromatic so as to form a polycycle (e.g., tetralin). An "arylene" group is a divalent analog of an aryl group. Aryl groups can also be fused or bridged with alicyclic or heterocyclic rings which are not aromatic so as to form a polycycle (e.g., tetralin).

The term "fused-ring structure" refers to two or more rings (e.g., aryl groups, carbocyclic groups, heterocyclic groups) that share at least one common side. Accordingly, when two substituents on a core structure are taken together to form a fused-ring structure, a common side may be the core ring structure. For example, if A and B in the structure

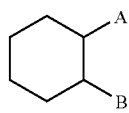

are taken together to form a fused-ring structure, exemplary resultant compounds include, but are not limited to, the following:

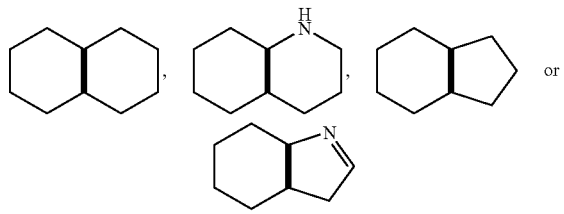

where the bond indicated in bold is the common side. As used herein, the term "7-16 membered fused-ring structure" refers to a fused ring having between 7 and 16 atoms comprising the ring.

The term "amine" or "amino," as used herein, refers to an unsubstituted or substituted moiety of the formula —NR$^a$R$^b$, in which R$^a$ and R$^b$ are each independently hydrogen, alkyl, aryl, or heterocyclyl, or R$^a$ and R$^b$, taken together with the nitrogen atom to which they are attached, form a cyclic moiety having from 3 to 8 atoms in the ring. Thus, the term "alkylamino" as used herein means an alkyl group having an amino group attached thereto. The term amino includes compounds or moieties in which a nitrogen atom is covalently bonded to at least one carbon or heteroatom. The term "dialkylamino" includes groups wherein the nitrogen atom is bound to at least two alkyl groups.

The term "alkylthio" refers to an alkyl group, having a sulfur group attached thereto. The term "alkoxy" as used herein means an alkyl group having an oxygen atom attached thereto. Examples of alkoxy groups include methoxy, ethoxy, isopropyloxy, propoxy, butoxy, and pentoxy groups.

The term "acyl" refers to a carbonyl group that is attached through its carbon atom to a hydrogen (i.e., a formyl), an aliphatic group (e.g., acetyl), an aromatic group (e.g., benzoyl), and the like. That is, acyl refers to a group devised from a carboxylic acid (RC(O)OH) with the following general formula: R—C(O)—, wherein R is a alkyl or aryl as defined herein. When R is an alkyl group, the "acyl" is equivalent to "alkylcarbonyl"; when R is an aryl group, the "acyl" is equivalent to "arylcarbonyl".

The term "nitro" means —NO$_2$; the term "halogen" or "halogeno" or "halo" designates —F, —Cl, —Br or —I; the term "thiol," "thio," or "mercapto" means —SH; the term "hydroxyl" or "hydroxy" means —OH; and the term "carboxylic acid" refers to —COOH.

It will be understood that "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, elimination, etc.

Copolymers of the Present Invention

In some aspects, the present invention is directed to a copolymer that includes (a) a plurality of constitutional units that correspond to at least one cationically polymerizable isomonoolefin species and (b) a plurality of constitutional units that correspond to at least one anionically polymerizable monomer species.

Some examples of cationically polymerizable isomonoolefin species include, but are not limited to, isomonoolefins with 4 to 18 carbon atoms per molecule, for example, isobutylene, 2-methylbutene, 3-methyl-1-butene, 4-methyl-1-pentene, beta-pinene, and the like. Accordingly, in some embodiments, the cationically polymerizable olefin species includes isobutylene, 2-methylbutene, 3-methyl-1-butene, 4-methyl-1-pentene and/or beta-pinene.

The anionically polymerizable monomer species includes monomers of formula (I):

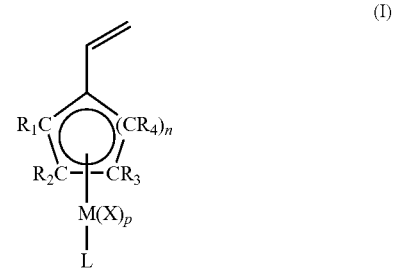

(I)

wherein
each independently selected from the group consisting of hydrogen, $C_1$-$C_{20}$ alkyl, $C_1$-$C_{20}$ alkyl substituted with $C_1$-$C_{20}$ aryl, $C_1$-$C_{20}$ aryl, halogen, $C_1$-$C_{20}$ haloalkyl, hydroxyl, $C_1$-$C_{20}$ alkoxy, amino, $C_1$-$C_{20}$ alkylamino, di($C_1$-$C_{20}$ alkyl)amino, thiol, $C_1$-$C_{20}$ alkylthio, carboxylate, $C_1$-$C_{20}$ acyl, nitro, cyano, or at least two R groups are taken together to form a fused ring structure;

n is an integer of 1 or 2;

p is an integer of 0 or 1;

M is a metal;

X is a counterion; and

L is one or more ancillary ligands.

In some embodiments, n is 1. That is, in some embodiments, the compound of formula I is a compound of formula I-a:

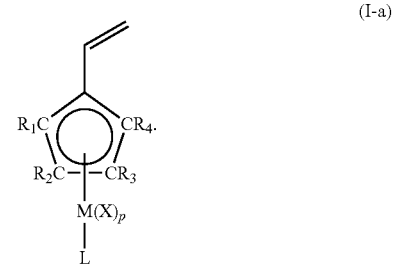

(I-a)

In other embodiments, n is 2. That is, in some embodiments, the compound of formula I is a compound of formula I-b:

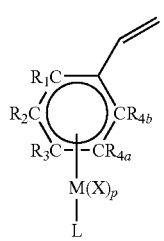

(I-b)

wherein $R_{4a}$ and $R_{4b}$ are each independently defined in the same manner as $R_4$ throughout the present application.

In compounds of formula (I), the vinyl substituent on the cyclopentadienyl or benzyl moiety forms the backbone of the polymer, e.g., to form a polymer which includes the following structure:

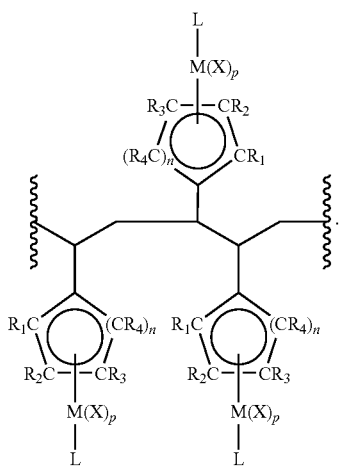

In some embodiments, $R_1$ is hydrogen. In some embodiments, $R_2$ is hydrogen. In some embodiments, $R_3$ is hydrogen. In some embodiments, $R_4$ is hydrogen. In some embodiments, only one of $R_1$, $R_2$, $R_3$ and $R_4$ is a group other than hydrogen. In some embodiments, at least one of $R_1$, $R_2$, $R_3$ and $R_4$ is a group other than hydrogen. In some embodiments, at least two of $R_1$, $R_2$, $R_3$ and $R_4$ are a group other than hydrogen. In some embodiments, at least three of $R_1$, $R_2$, $R_3$ and $R_4$ are a group other than hydrogen. In some embodiments, $R_1$, $R_2$, $R_3$ and $R_4$ are each a group other than hydrogen.

In some embodiments, two or more of $R_1$, $R_2$, $R_3$ and each occurrence of $R_4$ are taken together to form a 7-16 membered fused-ring structure. In some embodiments, two or more of $R_1$, $R_2$, $R_3$ and each occurrence of $R_4$ are taken together to form a 9-12 membered fused-ring structure. In an exemplary embodiment, $R_1$ and $R_2$ are taken together to form a fused ring structure and $R_3$ and each occurrence of $R_4$ are selected from hydrogen, $C_1$-$C_{20}$ alkyl, $C_1$-$C_{20}$ alkyl substituted with $C_1$-$C_{20}$ aryl, $C_1$-$C_{20}$ aryl, halogen, $C_1$-$C_{20}$ haloalkyl, hydroxyl, $C_1$-$C_{20}$ alkoxy, amino, $C_1$-$C_{20}$ alkylamino, di($C_1$-$C_{20}$ alkyl)amino, thiol, $C_1$-$C_{20}$ alkylthio, carboxylate, $C_1$-$C_{20}$ acyl, nitro or cyano. In another exemplary embodiment, $R_2$ and $R_3$ are taken together to form a fused ring structure and $R_1$ and each occurrence of $R_4$ are selected from hydrogen, $C_1$-$C_{20}$ alkyl, $C_1$-$C_{20}$ alkyl substituted with $C_1$-$C_{20}$ aryl, $C_1$-$C_{20}$ aryl, halogen, $C_1$-$C_{20}$ haloalkyl, hydroxyl, $C_1$-$C_{20}$ alkoxy, amino, $C_1$-$C_{20}$ alkylamino, di($C_1$-$C_{20}$ alkyl)amino, thiol, $C_1$-$C_{20}$ alkylthio, carboxylate, $C_1$-$C_{20}$ acyl, nitro or cyano. In an exemplary embodiment, $R_1$ and $R_2$ are taken together to form a fused ring structure and $R_3$ and an occurrence of $R_4$ are taken together to form a fused ring structure. In some embodiments the fused-ring structure is an alicyclic fused ring structure. In other embodiments, the fused-ring structure is a heterocyclic fused ring structure. In still other embodiments, the fused-ring structure is an aromatic fused ring structure.

The one or more ancillary ligands, L, are not meant to be limited as long as they do not interfere with the synthesis of the polymeric blocks of the present invention, e.g., by sufficiently changing the electronic properties of the vinyl group that participates in the polymerization. That is, the purpose of the ancillary ligand(s) is to ensure that the monomer is a stable (typically 18 electron) complex as described below. Exemplary ancillary ligands include, but are not limited to, the following:

a. one electron ligands such as alkyl ligands (-alkyl) or halogens;
b. two electron ligands such as carbonyl ligands (—CO), alkenes, carbenes or phosphines (—$PR_3$);
c. three electron ligands such as $\eta^3$-allyl or $\eta^3$-cyclopropenyl ligands;
d. four electron ligands such as dienes or $\eta^4$-cyclobutadienyl ligands;
e. five electron ligands such as $\eta^5$-cyclopentadienyl ligands, optionally substituted with $C_1$-$C_{20}$ alkyl, halogen, $C_1$-$C_{20}$ haloalkyl, hydroxyl, $C_1$-$C_{20}$ alkoxy, amino, $C_1$-$C_{20}$ alkylamino, di($C_1$-$C_{20}$ alkyl)amino, thiol, $C_1$-$C_{20}$ alkylthio, carboxylate, $C_1$-$C_{20}$ acyl, nitro or cyano; and
f. six electron ligands such as $\eta^6$-arene ligands, optionally substituted with $C_1$-$C_{20}$ alkyl, halogen, $C_1$-$C_{20}$ haloalkyl, hydroxyl, $C_1$-$C_{20}$ alkoxy, amino, $C_1$-$C_{20}$ alkylamino, di($C_1$-$C_{20}$ alkyl)amino, thiol, $C_1$-$C_{20}$ alkylthio, carboxylate, $C_1$-$C_{20}$ acyl, nitro or cyano.

It is noted that, in the above naming convention, the number following the $\eta$ refers to the number of carbons with which the metal is bonded via sharing of pi electrons.

In some embodiments, L is a ligand of formula (II):

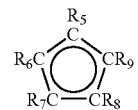

wherein $R_5$, $R_6$, $R_7$, $R_8$ and $R_9$ are each independently selected from the group consisting of hydrogen, $C_1$-$C_{20}$ alkyl, $C_1$-$C_{20}$ alkyl substituted with $C_1$-$C_{20}$ aryl, $C_1$-$C_{20}$ aryl, halogen, $C_1$-$C_{20}$ haloalkyl, hydroxyl, $C_1$-$C_{20}$ alkoxy, amino, $C_1$-$C_{20}$ alkylamino, di($C_1$-$C_{20}$ alkyl)amino, thiol, $C_1$-$C_{20}$ alkylthio, carboxylate, $C_1$-$C_{20}$ acyl, nitro, cyano, or at least two R groups are taken together to form a fused ring structure.

In some embodiments, $R_5$ is hydrogen. In some embodiments, $R_6$ is hydrogen. In some embodiments, $R_7$ is hydrogen. In some embodiments, $R_9$ is hydrogen. In some embodiments, $R_9$ is hydrogen. In some embodiments, only one of $R_5$, $R_6$, $R_7$, $R_8$ and $R_9$ is a group other than hydrogen. In some embodiments, at least one of $R_5$, $R_6$, $R_7$, $R_8$ and $R_9$ is a group other than hydrogen. In some embodiments, at least two of $R_5$, $R_6$, $R_7$, $R_8$ and $R_9$ are a group other than hydrogen. In some embodiments, at least three of $R_5$, $R_6$, $R_7$, $R_8$ and $R_9$ are a group other than hydrogen. In some embodiments, at least four of $R_5$, $R_6$, $R_7$, $R_8$ and $R_9$ are a group other than hydrogen. In some embodiments, $R_5$, $R_6$, $R_7$, $R_8$ and $R_9$ are each a group other than hydrogen.

In some embodiments, two or more of $R_5$, $R_6$, $R_7$, $R_8$ and $R_9$ are taken together to form a 7-16 membered fused-ring structure. In some embodiments, two or more of $R_5$, $R_6$, $R_7$, $R_8$ and $R_9$ are taken together to form a 9-12 membered fused-ring structure. In some embodiments the fused-ring structure is an alicyclic fused ring structure. In other embodiments, the fused-ring structure is a heterocyclic fused ring structure. In still other embodiments, the fused-ring structure is an aromatic fused ring structure.

In some embodiments, M is a transition metal. As used herein, the term "transition metal" refers to metals of groups 3-12 of the periodic table, e.g., element numbers 21-30, 39-48 and 57-80. In some embodiments, M is a transition metal selected from Fe, Mn, Cr, V, Co, Mo, Re, W, Ni, Ru, Ti, Zr or Os. In other embodiments, M is a metal selected from Fe, Co, Ni, Ru, Ti, Zr or Os. In still other embodiments, M is Fe. Transition metals typically have an oxidation state, which can typically be 0, +1, +2, +3 or +4. For example, a typical oxidation state of iron (Fe) is +2. In another example, a typical oxidation state of manganese (Mn) is +1. A transition metal may have more than one oxidation state. Oxidation states of metals, e.g., transition metals, are well known in the art for each transition metal.

The oxidation state of the metal M does not necessarily refer to the charge attributed to the complex as a whole, but rather the charge attributed to the metal. The charge from the oxidation state of the metal can be balanced as described in more detail below by, for example, the counterion X, the one or more ancillary ligands (L) and/or the portion of the compound of formula (I) which is drawn as:

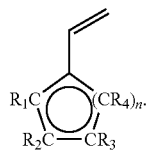

In such a convention, the skilled artisan understands that a cyclopentadienyl moiety (i.e., where n is 1 in the compounds of formula (I)) has an overall charge of −1, but that a benzyl moiety (i.e., where n is 2 in the compounds of formula (I)) has no overall charge.

In some embodiments, X is the counterion of the entire organometallic complex. In some embodiments, the counterion is employed to maintain electroneutrality. That is, in some embodiments, the organometallic complex is neutral, and no counterion is employed. In such cases, p is 0 in formula (I). In other embodiments, the organometallic complex has a charge, e.g., a net positive charge. In such cases, a counterion may be employed and thus p is 1 in formula (I). In some embodiments, the charge of the counterion is sufficient to neutralize the charge of the organometallic complex as a whole, e.g., if the complex carries a net charge of +2, then $x^-$ can be −2. Examples of anionic counter ions include, but are not limited to, halide, triflate, sulfate, nitrate, hydroxide, carbonate, bicarbonate, acetate, phosphate, oxalate, cyamide, alkylcarboxylate, N-hydroxysuccinimide, N-hydroxybenzotriazole, alkoxide, thioalkoxide, alkane sulfonyloxy, halogenated alkane sulfonyloxy, arylsulfonyloxy, bisulfate, oxalate, valerate, oleate, palmitate, stearate, laurate, borate, tetrafluoroborate, benzoate, lactate, citrate, maleate, fumarate, succinate, tartrate, naphthylate mesylate, glucoheptonate, or lactobionate.

The chemical structures herein are drawn according to the conventional standards known in the art. Thus, where an atom, such as a carbon atom, as drawn appears to have an unsatisfied valency, then that valency is assumed to be satisfied by a hydrogen atom even though that hydrogen atom is not necessarily explicitly drawn.

Additionally, the organometallic complexes herein are drawn according to the conventional standards known in the art. See, e.g., Bochman, M. *Organometallics I*, New York: Oxford University Press, 1994. Regarding the drawing convention,

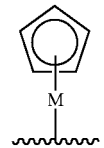

indicates that the metal M is sharing pi electrons with each of the carbons in the ring structure.

In terms of the valency of the metals included in the compounds of the present invention, it is understood that 18 electrons are generally required to fill the orbitals of a typical transition metal. Thus, unless specified otherwise, the organometallic complexes herein satisfy the 18-Electron Rule, which states that a stable complex occurs when the sum of the electrons donated from all ligands, the metal d electrons and the overall charge of the complex is equal to 18. For example, in the case of ferrocene, the two negatively charged cyclopentadienyl ligands each donate 6 electrons and $Fe^{2+}$ is a $d^6$ transition metal. Thus, the overall charge of the complex is 0 and the total number of electrons is 18.

Exemplary monomers of formula (I) include, but are not limited to vinylferrocene, vinylcobaltocene, vinylnickelocene, vinylruthenocene, vinyltitanocene, vinylzirconocene, and vinylosmocene.

In some embodiments, the anionically polymerizable monomer species comprises vinylferrocene. In some embodiments, the cationically polymerizable isomonoolefin species comprises isobutylene.

In some embodiments, the plurality of constitutional units that correspond to at least one cationically polymerizable isomonoolefin species comprises a plurality of constitutional units that correspond to a single cationically polymerizable isomonoolefin species. In other embodiments, the plurality of constitutional units that correspond to at least one cationically polymerizable isomonoolefin species comprises a plurality of constitutional units that correspond to two or more cationically polymerizable isomonoolefin species.

In some embodiments, the plurality of constitutional units that correspond to at least one anionically polymerizable monomer species comprises a plurality of constitutional units that correspond to a single anionically polymerizable monomer species. In other embodiments, the plurality of constitutional units that correspond to at least one anionically polymerizable monomer species comprises a plurality of constitutional units that correspond to two or more anionically polymerizable monomer species.

The copolymers of the present invention may be block copolymers. Accordingly, in some embodiments, the plurality of constitutional units that correspond to at least one anionically polymerizable monomer species is a polymer block and the plurality of constitutional units that correspond to at least one anionically polymerizable monomer species is a polymer block. The copolymers of the present invention can include any number of polymer block, e.g., can be a diblock copolymer, a triblock copolymer, or may have four or more (e.g., 5, 6, 7, 8, 9 or 10) blocks. In some embodiments, the copolymers of the present invention include more than 10 blocks. In some embodiments, the copolymers of the present invention are diblock copolymers. In other embodiments, the copolymers of the present invention are triblock copolymers.

The copolymers of the present invention also embrace a variety of configurations, including linear and branched configurations. Branched configurations include radial configurations, star-shaped configurations (e.g., configurations in which three or more chains emanate from a single region), comb configurations (e.g., graft copolymers having a main chain and a plurality of side chains), and dendritic configurations (e.g., arborescent or hyperbranched copolymers).

In some embodiments, the number average molecular weight of the poly(vinylmetallocene) ranges from about 100 to about 500,000. In other embodiments, the number average molecular weight of poly(vinylmetallocene) ranges from about 500 to about 100,000. In some embodiments, the copolymers of the present invention have a number average molecular weight ranging from about 200 to about 2,000,000. In other embodiments, the copolymers of the present invention have a number average molecular weight ranging from about 500 to about 500,000. In still other embodiments, the copolymers of the present invention have a number average molecular weight ranging from about 10,000 to about 100,000.

The ratio of constitutional units corresponding to the cationically polymerized monomers (e.g., isobutylene) relative to the constitutional units corresponding to the anionically polymerized monomers (e.g., compounds of formula (I)) in the copolymer usually ranges from 1/99 to 99/1 w/w, preferably from 30/70 to 95/5 w/w. In some embodiments, copolymers are provided which have a narrow molecular weight distribution such that the ratio of weight average molecular weight to number average molecular weight (Mw/Mn) (i.e., the polydispersity index) of the polymers ranges from about 1 to about 10. In some embodiments, the polydispersity index of the copolymers of the present invention range from about 1 to about 2.

Synthesis of Copolymers of the Present Invention

In some aspects, the present invention is directed to methods of making block copolymers as described herein, e.g., copolymers which include polyisomonoolefin and a polymer comprising monomer units of formula (I), (e.g., poly(vinylmetallocene)).

The copolymers of the present invention can be prepared via the combination of living cationic polymerization and living anionic polymerization. Hence, copolymers containing one or more cationically polymerized blocks and one or more anionically polymerized blocks can be formed.

The method generally includes contacting an end functionalized polyisomonoolefin with a living organometallic polymer in the presence of an initiator. The living organometallic polymer includes a plurality of constitutional units that correspond to at least one anionically polymerizable monomer species selected from the group consisting of monomers of formula (I):

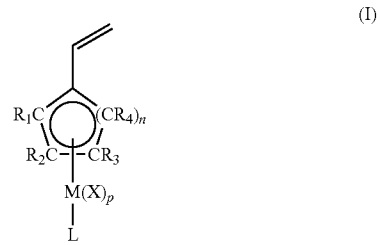

wherein
R$_1$, R$_2$, R$_3$ and each occurrence of R$_4$ are each independently selected from the group consisting of hydrogen, C$_1$-C$_{20}$ alkyl, C$_1$-C$_{20}$ alkyl substituted with C$_1$-C$_{20}$ aryl, C$_1$-C$_{20}$ aryl, halogen, C$_1$-C$_{20}$ haloalkyl, hydroxyl, C$_1$-C$_{20}$ alkoxy, amino, C$_1$-C$_{20}$ alkylamino, di(C$_1$-C$_{20}$ alkyl)amino, thiol, C$_1$-C$_{20}$ alkylthio, carboxylate, C$_1$-C$_{20}$ acyl, nitro, cyano, or at least two R groups are taken together to form a fused ring structure;
n is an integer of 1 or 2;
p is an integer of 0 or 1;
M is a metal;
X is a counterion; and
L is one or more ancillary ligands.

Exemplary instances of R$_1$, R$_2$, R$_3$, R$_4$, n, p, M, X, and L include any of the variables given in connection with the copolymers of the present invention. For example, in some embodiments, the monomer of formula (I) includes vinylferrocene, vinylcobaltocene, vinylnickelocene, vinylruthenocene, vinyltitanocene, vinylzirconocene, and/or vinylosmocene.

As discussed in connection with the monomers of formula (I), R$_1$-R$_9$ may be a functional group, e.g., a hydroxyl, a carboxy, a formyl, an amine or a thiol. In such embodiments, these groups may be protected with a suitable protecting group prior to anionic polymerization. The term "protecting group" as used herein, refers to the functional moiety, e.g., O, S, or N, being temporarily blocked so that a reaction can be carried out selectively at another reactive site in a multifunctional compound. Exemplary oxygen protecting groups include, but are not limited to methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether)), substituted ethyl ethers, substituted benzyl ethers, silyl ethers (e.g., TMS (trimethylsilyl ether), TES (triethylsilyl ether), TIPS (triisopropylsilyl ether), TBDMS (tert-butyldimethylsilyl ether), tribenzyl silyl ether, TBDPS (tert-butyldiphenylsilyl ether)), esters (e.g., formate, acetate, benzoate (Bz), trifluoroacetate, dichloroacetate), carbonates, cyclic acetals and ketals. Exemplary nitrogen protecting groups include, but are not limited to, carbamates (including methyl, ethyl and substituted ethyl carbamates (e.g., Troc)) amides, cyclic imide derivatives, N-Alkyl and N-Aryl amines, N-silyl amines, imine derivatives, and enamine derivatives. The present invention is not intended to be limited to these protecting groups; rather, a variety of additional equivalent protecting groups can be readily identified and utilized in the present invention. For example, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

As used herein, the term "end functionalized polyisomonoolefin" refers to a polyisomonoolefin as described herein, which has at least one end that has been adapted such that it can undergo polymerization with a living organometallic polymer as described herein. The polyisomonoolefin can also be a polyisomonoolefin with 4 to 18 carbon atoms per isomonoolefin monomer, for example, isobutylene, 2-methylbutene, 3-methyl-1-butene, 4-methyl-1-pentene, beta-pinene, and the like.

In order to provide an end-functionalized polyisomonoolefin, one or more of the ends of the polyisomonoolefin is adapted with any functional group which allows the polyisomonoolefin to subsequently undergo polymerization with a living organometallic polymer. Accordingly, in some embodiments, the end functionalized polyisomonoolefin is an haloallyl end-functionalized polyisomonoolefin, e.g., an iodoallyl, chloroallyl or an bromoallyl end-functionalized polyisomonoolefin. In certain embodiments, the end-functionalized polyisomonoolefin is an bromoallyl end-functionalized polyisomonoolefin. In other embodiments, the end-functionalized polyisomonoolefin is a halosilyl end-functionalized polyisomonoolefin, e.g., a chlorosilyl end-functionalized polyisomonoolefin.

Allyl and haloallyl end-functionalized polyisonomoolefins can be prepared using known methods, such as the methods described, e.g., in (a) Higashihara, T. et al. *Macromolecules* 2006, 39, 5275-9, (b) Györ, M. et al. *J. Macromol. Sci., Pure Appl. Chem.* 1992, A29, 639-53, (c) De. P. et al. *Macromolecules* 2006, 39, 6861-70, (d) Wilczek, L. et al. *J. Polym. Sci., Part A: Polym. Chem.* 1987, 25, 3255-65 and/or (e) Ivan, B. et al. *J. Polym. Sci., Part A: Polym. Chem.* 1990, 28, 89-104.

Halosilyl end-functionalized polyisonomoolefins can be prepared by hydrosilation of allyl end-functionalized polyisoolefin with silyl hydride compounds. The precursor, allyl end-functionalized polyisoolefin, can be prepared using known methods, such as the methods described, e.g., (a) Wilczek, L. et al. *J. Polym. Sci., Part A: Polym. Chem.* 1987, 25, 3255-65. (b) Iván, B. et al. *J. Polym. Sci., Part A: Polym. Chem.* 1990, 28, 89-104. In some embodiments, silyl hydride compounds have the formula $XSiHR_1R_2$ where X is chlorine, bromine, or iodine and $R_1$ and $R_2$ are alkyl group containing 1 to 20 carbons, respectively. In some embodiments, silyl hydride compounds are used in concentrations of 1 to 100 times higher than that of allyl functionality. In other embodiments, silyl hydride compounds are used in concentrations of 5 to 20 times higher than that of polymer. Transition metal complexes such as those which include platinum, rhodium, ruthenium, iridium, osmium, and palladium are employed as catalysts for hydrosilation. In some embodiments, platinium (IV) catalyst, $H_2PtCl_6$ or platinium (O) catalyst, $Pt_2[CH_2=CHSi(CH_3)_2OSi(CH_3)_2CH=CH_2]$ is used in hydrosilation. In some embodiments, the catalyst is used in concentrations of 1 to 1000 ppm versus the polymer by weight. In other embodiments, the catalyst is used in concentrations of 10 to 300 ppm.

In some embodiments, the end functionalized polyisomonoolefin is bromoallyl end-functionalized polyisobutylene. In other embodiments, the end functionalized polyisomonoolefin is chlorosilyl end-functionalized polyisobutylene.

In some embodiments, diblock copolymers, triblock copolymers and/or radial-shaped block copolymers are prepared using monofunctional, difunctional or multifunctional polymers, respectively. In some embodiments, end functionalized polyisomonoolefins are used to synthesize multifunctional polymers, e.g., star polymers such as polyisobutylene stars, for example, by reacting the polyisomonoolefins with coupling molecules such as unhindered chlorosilanes. Chlorosilanes have been used previously to couple living anionic chain ends to form star polymers in Roovers, J. E. L. and S. Bywater, *Macromolecules* 1972, 5, 385 and in U.S. Application Publication No. 20050143526. Triblock copolymers and radial-shaped block copolymers typically exhibit elastomeric properties which are dependant upon the composition of polyisomonolefin and organometallic polymer segments in the block copolymers.

As used herein, the term "living organometallic polymer" refers to an organometallic polymer that does not have the ability to chain to terminate. Accordingly, in some embodiments, the end functionalized polyisomonoolefin is added to the living organometallic polymer which comprises monomers of formula (I).

The synthesis of copolymers of the present invention is carried out in the presence of an initiator. In some embodiments, the initiator is used to initiate living polymerization of the monomers of formula (I). The end-functionalized polyisomonoolefin can then be introduced to the system to form the copolymer. Typically, the initiator is an organometallic compound, including but not limited to a wide range of organoalkali compounds of the formula RM in which R is a hydrocarbon compound containing from 1 to 20 carbon atoms per molecule and M is an alkali metal selected from lithium, sodium, potassium, or cesium. Hydrocarbon groups of R can be selected, for example, from unbranched alkyl groups, branched alkyl groups, cyclic alkyl groups, mono-ring aryl groups and multi-ring aryl groups. Examples of suitable organometallic compounds include, but are not limited to, methyllithium, ethyllithium, isopropyllithium, n-butyllithium, sec-butyllithium, tert-butyllithium, tert-octyllithium, phenyllithium, 1-naphthyllithium, p-tolyllithium, cyclohexyllithium, 4-cyclohexylbutyllithium, potassium naphthalenide, sodium naphthalenide, and cesium naphthalenide. In some embodiments, the organometallic compound is butyllithium. In some embodiments, the organoalkali compound is used at concentrations that are 1 to 50 times the concentration of the end-functionalized polyisomonoolefin concentration. In other embodiments, the organoalkali compound is used at concentrations that are 1 to 10 times the polyisomonoolefin concentration.

In some embodiments, other suitable initiators and/or coinitiators may be used, including, but not limited to an alkyl lithium or an aryl lithium compound containing 1 to 20 carbons with a protected functional group (e.g., a hydroxyl, a carboxy, a formyl, an amine and a thiol), a lithium amide with a formula of $LiNR_1R_2$ where $R_1$ and $R_2$ are each independently an alkyl group or an aryl group containing 1 to 20 carbons (e.g., lithium N,N-diisopropylamide), a hydride compound (e.g., lithium aluminum hydride, sodium hydride), a Grignard reagent with a formula of RMgX where R is an alkyl group or an aryl group containing 1 to 20 carbons and X is chlorine, bromine, or iodine, respectively. Initiators may be monofunctional, difunctional, trifunctional and so forth, thereby producing, for example, diblock copolymers, triblock copolymers, and radial-shaped block copolymers, respectively. Such initiators can be found, for example, in U.S. Pat. No. 7,056,985.

In some embodiments, the molar ratio of living organometallic polymer/end functionalized polyisomonoolefin ranges from about 1/3 to about 3/1. In other embodiments, the molar ratio of living organometallic polymer/end functionalized polyisomonoolefin ranges from about 1/1 to about 1.8/1.

The various reactions of the present invention are typically carried out in the presence of a diluent or a mixture of diluents. For example, the polymerization of the isomonoolefin is typically carried out in a diluent or a mixture of diluents, which include (a) halogenated hydrocarbons which contain from 1 to 4 carbon atoms per molecule, such as methyl chloride and methylene dichloride, (b) aliphatic hydrocarbons and cycloaliphatic hydrocarbons which contain from 5 to 8 carbon atoms per molecule, such pentane, hexane, heptane, cyclohexane and methyl cyclohexane, or (c) mixtures thereof. The hydrosilation of the isomonoolefin is typically carried out in the presence of diluent or mixture of diluents, including aromatic hydrocarbons which contain from 1 to 20 carbon atoms per molecule, ethers which include tetrahydrofuran, ether, dioxane, and 1,2-dimethoxyethane, or mixtures thereof. Additionally, the polymerization of the monomers of formula (I), e.g., vinylmetallocene monomers, as well as the coupling of the haloallyl end-functionalized polyisomonoolefin or the halosilyl end-functionalized polyisomonoolefin with the living organometallic polymer comprising monomers of formula (I), e.g., vinylmetallocene, is typically carried out in the presence of a diluent or mixture of diluents including, but not limited to, ethers such as tetrahydrofuran, ether, dioxane, and 1,2-dimethoxyethane.

The various reactions of the present invention are typically carried out under varying temperatures for varying periods of time. For example, in some embodiments, temperatures employed in the polymerization of the isomonoolefin range from 0° C. to −150° C. In other embodiments, temperatures employed in the polymerization of the isomonoolefin range from −10° C. to −90° C. In some embodiments, the reaction time for the polymerization of the isomonoolefin ranges from a few minutes to 24 hours. In other embodiments, the reaction time for the polymerization of the isomonoolefin ranges from 10 minutes to 10 hours.

In some embodiments, temperatures employed in the hydrosilation of the isomonoolefin range from 25° C. to 200° C. In other embodiments, temperatures employed in the hydrosilation of the isomonoolefin range from 25° C. to 120° C. In some embodiments, the reaction time for the hydrosilation ranges from 10 minutes to 48 hours. In other embodiments, the reaction time for the hydrosilation ranges from 1 hour to 12 hours.

In some embodiments, temperatures employed in the polymerization of monomers of formula (I), e.g., vinylmetallocene monomers, range from 50° C. to −100° C. In some embodiments, temperatures for the polymerization of monomers of formula (I) range from 10° C. to −40° C. In some embodiments, reaction time of the polymerization of monomers of formula (I) ranges from 1 hour to 96 hours. In other embodiments, reaction time of the polymerization of monomers of formula (I) ranges from 2 hours to 24 hours.

In some embodiments, temperatures for the coupling of the haloallyl end-functionalized polyisomonoolefin or the halosilyl end-functionalized polyisomonoolefin with the living organometallic polymer comprising monomers of formula (I), e.g., vinylmetallocene, range from 50° C. to −80° C. In other embodiments, temperatures for the coupling reaction range from 10° C. to −40° C. In some embodiments, the reaction time for the coupling of the haloallyl end-functionalized polyisomonoolefin with the living organometallic polymer comprising monomers of formula (I), e.g., vinylmetallocene, ranges from 1 hour to 96 hours. In other embodiments, the reaction time for the coupling reaction ranges from 4 hours to 24 hours. In some embodiments, the reaction time for the coupling of the halosilyl end-functionalized polyisomonoolefin with the living organometallic polymer comprising monomers of formula (I), e.g., vinylmetallocene, ranges from 1 minute to 48 hours. In other embodiments, the reaction time for the coupling reaction ranges from 30 minutes to 24 hours.

In some embodiments, a proton scavenger, e.g., a Lewis base for the polymerization of isomonoolefin, is included in the reaction in an attempt to prevent protic impurities, such as water. Such impurities can lead to polymeric contaminants in the final product. Examples of proton scavengers (also referred to as proton traps) include sterically hindered pyridines, for example, substituted or unsubstituted 2,6-di-tert-butylpyridines, such as 2,6-di-tert-butylpyridine and 4-methyl-2,6-di-tert-butylpyridine, as well as 1,8-bis(dimethylamino)-naphthalene and diisopropylethyl amine. The proton trap is usually used at the concentration of 1 to 10 times higher than that of protic impurities in the polymerization system.

In some embodiments, the method of the present invention further comprises contacting the polymerization zone with degassed alcohol in order to quench the system. In other embodiments, the method of the present invention further comprises contacting the polymerization zone with chlorotrimethylsilane in order to quench the system. The "polymerization zone" refers to the reaction mixture which includes an end functionalized polyisomonoolefin and a living organometallic polymer.

In some embodiments, the end-functionalized polyisomonoolefins of the present invention are used to efficiently couple with a living polymer of anionically polymerizable monomer species yielding block copolymers with high blocking efficiency. The "coupling efficiency" (c.e.) is the percentage of polyisomonoolefins that were actually coupled with the living polymer. The resulting block copolymers, e.g., diblock polymers, triblock copolymers, radial-shaped block copolymers, etc., will exhibit properties that depend upon the cationically and anionically polymerizable species found within the block copolymer, as well as their absolute and relative amounts.

In other embodiments of the invention, block copolymers are reacted (subsequent to anionic polymerization and before anion quenching) with coupling molecules such as (di- or trichloromethyl)benzene or (di- or tribromomethyl)benzene, thereby forming larger-scale copolymers (See, e.g., U.S. Application Publication No. 20050143526).

Articles of Manufacture

In some aspects, the present invention is directed to articles of manufacture which include the copolymers described herein. For example, the block copolymers of the present invention can be employed as new thermoplastic elastomers, electronic device materials, biomaterials and other polymeric materials.

In some embodiments, the article of manufacture is an insertable or implantable medical device, e.g., a catheter, an endotracheal tube, a tracheostomy tube, a wound drainage device, a wound dressing, a stent, an implant, an intravenous catheter, a medical adhesive, a suture, a shunt, a gastrostomy tube, medical tubing, cardiovascular products, heart valves, pacemaker leads, a guidewire, or urine collection devices.

In some embodiments, the articles of manufacture include medical devices from which a therapeutic agent is released. Such therapeutic agents may be, e.g., trapped within the polymer system or attached to the polymer itself (e.g., via ionic or covalent attachment). In such embodiments where the therapeutic agent is attached to the polymer itself, it is understood that the therapeutic agent will have a release profile (e.g., is able to be released via, for instance, hydrolysis or enzymatic cleavage. Accordingly, in some embodiments, compositions of the present invention include a therapeutic agent and exhibit an appropriate release profile. Such compositions and materials are also useful as medical drug eluting articles and drug eluting coatings.

In some embodiments, the article of manufacture is an electronic device.

In some embodiments, copolymers of the invention can be dried and melt processed, for example, by injection molding and extrusion. Compositions used for this method can be used alone or compounded with any other melt-processable material for molding and extrusion of antimicrobial articles.

The copolymers of the invention can also be coated onto preformed articles. When used as a coating, the copolymers can be applied by any means, including those methods known in the art. For example, a composition comprising the copolymers of the invention can be brushed or sprayed onto the article from a solution, or the article can be dipped into the solution containing the copolymers of the invention.

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The contents of all references, patents, and patent applications cited throughout this application are hereby incorporated herein by this reference.

EXEMPLIFICATION

Materials

Reagents were obtained from Sigma-Aldrich Corp. unless otherwise stated.

Hexanes (Hex, Doe & Ingals, Technical grade) were refluxed for 48 hours with concentrated sulfuric acid. They were washed three times with 10% sodium hydroxide aqueous solution (NaOH aq.) and then with distilled water several times until neutral. After drying overnight over anhydrous sodium sulfate, they were refluxed under nitrogen overnight with calcium hydride ($CaH_2$) and distilled. For use in anionic polymerization, they were finally distilled over 1,1-diphenylhexyllithium (DPH-Li) on a vacuum line ($10^{-6}$ torr).

Acetone (Doe & Ingals, Technical grade) and methanol (Doe & Ingals, Technical grade) were purified by the distillation over potassium carbonate and activated magnesium, respectively.

Toluene (99%) was sequentially washed with concentrated sulfuric acid twice, 10% NaOH aq. once, and then with distilled water twice. After drying over calcium chloride and phosphorus pentoxide, it was refluxed over lithium aluminum hydride (LAH) under nitrogen and then distilled. Final distillation over DPH-Li on the vacuum line afforded pure dry toluene.

Anhydrous tetrahydrofuran (THF, 99.9%) was refluxed over LAH for 24 h under nitrogen and distilled. It was finally dried by the distillation over DPH-Li on the vacuum line. n-Butyllithium ("BuLi, FMC Lithium, 15 wt % solution in hexane) was used as received or after diluting with pure hexanes.

The active concentration of an "BuLi solution was determined by the polymerization of styrene.

Vinylferrocene (VFe, 97%) was purified by double sublimation, followed by the azeotropic distillation of a trace amount of water from its dry toluene solution three times.

Chlorotrimethylsilane (TMS-Cl, 99+%) and chlorodimethylsilane (DMS-Cl, 98%) were stirred with $CaH_2$ at 25° C. for 24 h, and then distilled under high vacuum.

Methyl chloride (MeCl, Airgas Inc.) and isobutylene (IB, Matheson Tri Gas) were dried in the gaseous state by passing them through in-line gas-purifier columns packed with barium oxide/drierite.

Titanium(IV) chloride ($TiCl_4$, 99.9%), 2,6-di-tert-butylpyridine (DTBP, 97%), 1,3-butadiene (99+%), lithium bromide (LiBr, anhydrous, >99%), sodium iodide (NaI, anhydrous, >99%), benzene (anhydrous, 99.8%), 2-butanone (>99%), and Karstedt's catalyst, $Pt_2[CH_2=CHSi(CH_3)_2OSi(CH_3)_2CH=CH_2]$, 2.1-2.4% in xylene (Gelest) were used as received.

5-tert-Butyl-1,3-bis(1-chloro-1-methylethyl)benzene (DicumylCl) was synthesized according to the procedure described, e.g., in Györ, M. et al. *J. Macromol. Sci., Pure Appl. Chem.* 1992, A29, 639-53.

Chloroallyl, bromoallyl, and allyl chain-end functionalized PIB (PIB-AllylCl, PIB-AllylBr, and PIB-Allyl), and α,ω-allyl di-functionalized PIB (Allyl-PIB-Allyl) were synthesized as described, e.g., in (a) Higashihara, T. et al. *Macromolecules* 2006, 39, 5275-9, (b) Györ, M. et al. *J. Macromol. Sci., Pure Appl. Chem.* 1992, A29, 639-53, (c) De. P. et al. *Macromolecules* 2006, 39, 6861-70, (d) Wilczek, L. et al. *J. Polym. Sci., Part A: Polym. Chem.* 1987, 25, 3255-65 and/or (e) Ivan, B. et al. *J. Polym. Sci., Part A: Polym. Chem.* 1990, 28, 89-104 and purified by the precipitation with hexanes/methanol twice, followed by the azeotropic distillation with dry toluene three times.

Measurements

Molecular weights and polydispersity indices (PDIs) were measured with a Waters HPLC system equipped with a model 510 HPLC pump, model 410 differential refractometer, model 441 absorbance detector (254 nm), online multiangle laser light scattering (MALLS) detector (MiniDawn, Wyatt Technology Inc.), model 712 sample processor, and five Ultrastyragel GPC columns connected in the following series: 500, $10^3$, $10^4$, $10^5$, and 100 Å. THF was used as a carrier solvent at a flow rate of 1.0 mL/min at room temperature. The dn/dc value of PVFe (5 K) is 0.248 measured by Optilab ESP refractometer (Wyatt Technology Inc.) in THF at 35° C. using a batch mode. Nuclear Magnetic Resonance (NMR) spectroscopy was carried out on a Bruker 500 MHz spectrometer using $CDCl_3$ as a solvent. $^1H$ NMR spectra of solutions in $CDCl_3$ were calibrated to tetramethylsilane (TMS) as internal standard ($\delta_H$ 0.00).

Example 1

Living Anionic Polymerization of Vinylferrocene

The polymerizations of VFe were carried out in THF at −28° C., 0° C., or 25° C. with "BuLi under high vacuum conditions (<$10^{-6}$ torr) in sealed glass reactors with breakseals. The reactors were pre-washed with a DPH-Li solution in hexanes after being sealed off from the vacuum line. Concentrations of "BuLi and VFe ranged from 0.00390-0.00890 M and 0.189-0.198 M, respectively. Solutions exhibited slight turbidity at all temperatures, likely due to the aggregation of high MW polyvinylferrocenes. In all cases, however, the insoluble part was less than 1 wt %. The polymerizations were quenched with degassed methanol or excess chlorotrimethylsilane (TMS-Cl).

For example, a hexane solution of $^n$BuLi (0.00577 M×1.54 mL=0.0889 mmol) was placed in an apparatus under high vacuum, followed by complete removal of the hexanes in vacuo. A stock solution of VFe (0.198 M×10.0 mL=1.98 mmol, 0.420 g) in THF was next added at 0° C. to start the polymerization. About half of the solution was removed from the reaction vessel by heat-sealing, and subsequently quenched with TMS-Cl (0.200 mmol) in hexanes (1.25 mL). The remainder of the solution was allowed to stand for an additional 3 h, then quenched with TMS-Cl (0.200 mmol) in hexanes (1.25 mL). The introduction of the TMS group at the chain end also acted as a probe in $^1$H NMR spectroscopy. After quenching, a few drops of a pyridine/methanol (50/50, v/v) mixture were immediately added to neutralize the solutions. The solutions were then filtrated to remove the insoluble parts (<1 wt %). The polymers were isolated by precipitation from their THF solution into methanol (THF/methanol=1/4, v/v), followed by freeze-drying with benzene to yield yellow powders. Conversions: 89% (1 hour) and 98% (4 hours) by $^1$H NMR. Yields: 0.174 g, 83% (1 h) and 0.193 g, 92% (4 h). $^1$H NMR (CDCl$_3$): δ 4.50-3.80 (br, ferrocenyl-H), 2.70-0.80 (br, CH$_2$ and CH), 0.40-0.19 (br, 9H, Si(CH$_3$)$_3$).

Figure 3A:
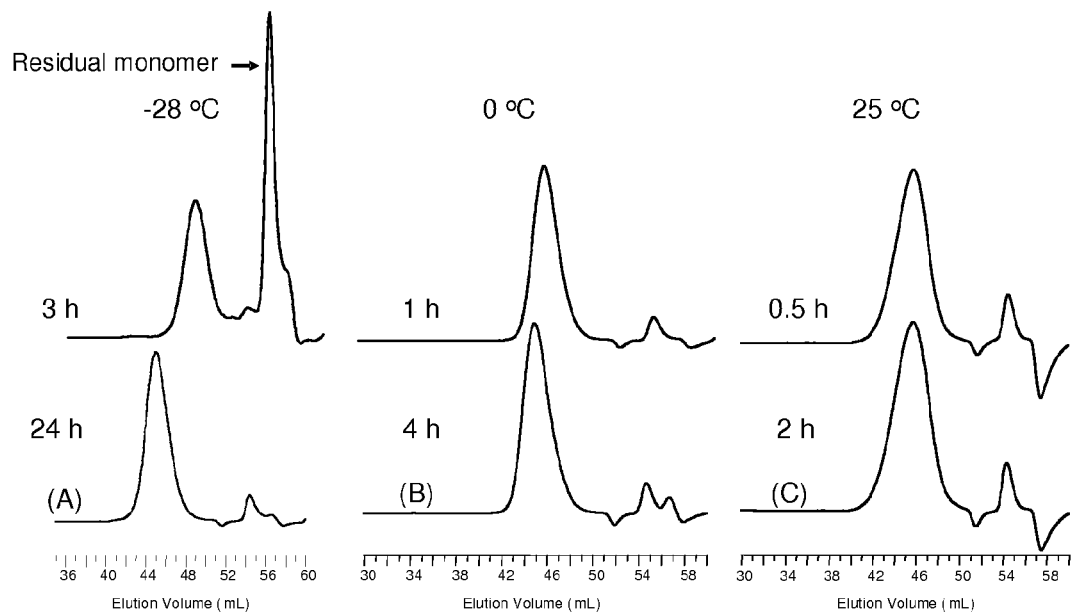
FIG. 3A is a graph depicting GPC RI traces of PVFes obtained at −28° C., 0° C., and 25° C.

FIG. 3A (A)-(C) show GPC RI traces of the poly(vinylferrocene)s thus obtained. Sharp and monomodal peaks corresponding to polyvinylferrocenes (PVFes) are observed in all cases. Polymers generated at −28° C. and 0° C. reached 95% and 98% conversions, respectively, while the polymer generated at 25° C. reached a limiting conversion of around 70%. During polymer formation, GPC RI peaks of polymers generated at −28° C. and 0° C. shift to higher MW region while maintaining their shapes and narrow distributions. Results and properties of polymers are summarized in Table 1.

believed that this may be caused by lithium hydride elimination at chain end or by chain transfer.

The results indicate that the anionic polymerization of VFe proceeded in a living manner at −28° C. and 0° C., with a target molecular weight of up to about 10,000. Thus PVFes can be formed using the methods of the present invention with predictable molecular weights and narrow PDIs. Although the anionic polymerization of VFe did not proceed to more than about 75% completion in a living manner at 25° C. under the present polymerization conditions, it is believed that a higher conversion may result from varying other reaction conditions.

Example 2

Synthesis of AB Diblock Copolymer by Coupling of Haloallyl End-functionalized Polyisobutylene with Living Poly(Vinylferrocene)

The synthesis of PIB-b-PVFe diblock copolymer was completed by employing haloallyl chain-end functionalized PIB (PIB-AllylX) series and living PVFe as outlined in FIG. 1. An apparatus equipped with the ampoules of stock solutions, $^n$BuLi in hexane, VFe in THF, bromoallyl end-functionalized polyisobutylene (PIB-AllylBr) in THF, and TMS-Cl in hexanes, washed with DPH-Li in hexanes solution. After the washing solution was discarded, $^n$BuLi (0.0714 mmol) in hexane was charged in the apparatus. Hexane was completely removed in vacuo, followed by the immediate addition a THF stock solution (8.0 mL) of VFe (0.26 g, 1.23 mmol) with stirring at 0° C. The solution was allowed to stand at 0° C. for

TABLE 1

Anionic Polymerization of VFe with $^n$BuLi in THF

| temp (° C.) | time (h) | conv. (%)[a] | $M_n$ (g/mol) calcd[b] | $M_n$ (g/mol) GPC-MALLS[c] | $M_n$ (g/mol) $^1$H NMR | PDI | fn[d] |
|---|---|---|---|---|---|---|---|
| −28 | 3 | 59 | 3,060 | 2,500 | — | 1.15 | — |
| −28 | 24 | 95 | 4,930 | 4,850 | — | 1.10 | — |
| 0 | 1 | 89 | 4,310 | 4,510 | — | 1.14 | — |
| 0 | 4 | 98 | 4,750 | 4,830 | 4,810 | 1.10 | 1.00 |
| 0 | 4 | 75 | 9,260 | 9,350 | — | 1.22 | — |
| 0 | 8 | 88 | 10,900 | 12,400 | 12,700 | 1.19 | 0.98 |
| 25 | 0.5 | 73 | 3,600 | 4,280 | — | 1.19 | — |
| 25 | 2 | 69 | 3,420 | 4,000 | 4,960 | 1.16 | 0.81 |

[a]Determined from $^1$H NMR by comparing the signal intensities at 5.02, 5.35, and 6.48 ppm attributed to the residual VFe and ones at 0.80~2.70 ppm attributed to PVFe.
[b]Calculated from the equation: $M_n$ (calcd) = 57.1 (C$_4$H$_9$) + 212.07 (VFe) × [VFe]/[$^n$BuLi] × conv. + X (X = 1 (H) or 73.09 (TMS)).
[c]dn/dc = 0.248.
[d]TMS chain-end functionality determined by the ratio, $M_n$ (GPC-MALLS)/$M_n$ ($^1$H NMR).

Figure 3B:
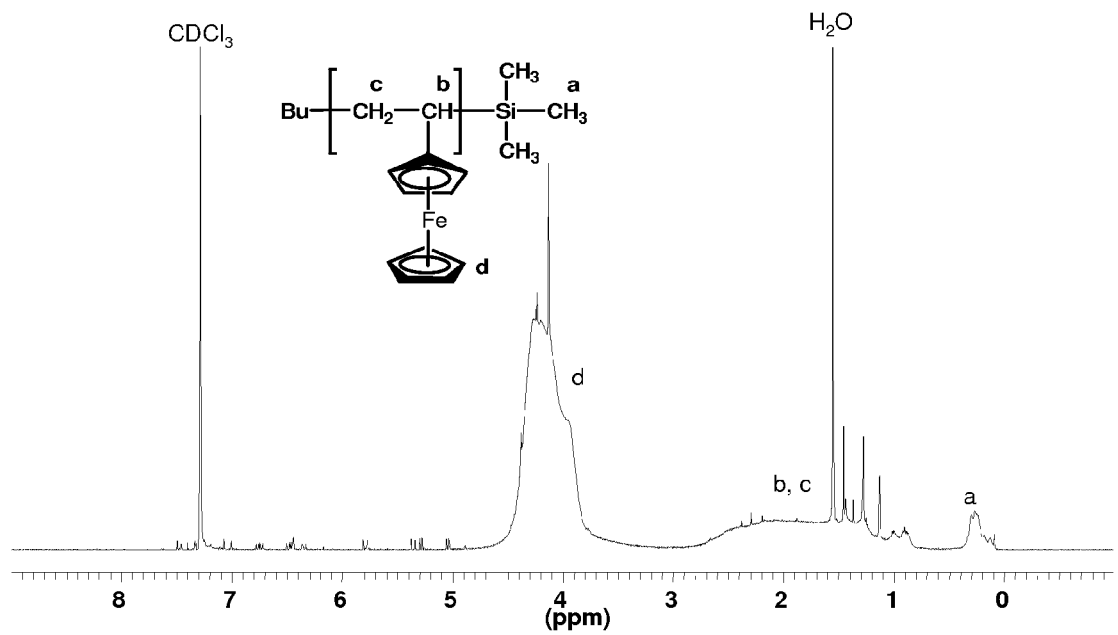
FIG. 3B is a $^1$H NMR spectrum of PVFe obtained in THF at 0° C. for 4 h.

The $M_n$ values measured by GPC-MALLS system are in good agreement with those calculated in all runs within the experimental error. The polydispersity indices (PDIs) are all narrow (1.1-1.2). The $M_n$ values for 0 and 25° C. were also determined from $^1$H NMR spectroscopy by comparing the signal intensities at 0.2 to 0.4 ppm assignable to the nine silylmethyl protons in the TMS group at the chain end and ones at 3.8 to 4.5 ppm assignable to the cyclopentadienyl protons in the PVFe main chain. FIG. 3B shows a representative $^1$H NMR spectrum of PVFe terminated with TMS group (0° C., $M_n$=4,810 g/mol). The $M_n$ values for two samples at 0° C. (4,810 and 12,700 g/mol) agree well with those measured by GPC-MALLS. In addition, the functionalities of the TMS group are virtually quantitative, clearly indicating that all chain ends are active. However, PVFe obtained at 25° C. shows less TMS-functionality (0.81). It is 4 hours. After a 20% portion of the solution was taken out by heat-sealing for characterizations, the THF stock solution (5.0 mL) of PIB-AllylBr ($M_n$=15,600, PDI=1.07, 0.37 g, 0.0237 mmol, bromoallyl functionality=1.00) was added to the rest and divided into two portions by heat-sealing. After 1 hour or 16 hours, the solutions were separately quenched with an excess of TMS-Cl (0.20 mmol). The concentrations are as follows; [$^n$BuLi]=0.00893 M and [VFe]=0.154 M for the polymerization, [living poly(vinylferrocene) (PVFeLi)]= 0.00449 M determined from $M_n$ (GPC-MALLS) and the amount of VFe consumed and [PIB-AllylBr]=0.00208 M for the coupling reaction. A few drops of pyridine/methanol (50/50, v/v) mixture were immediately added, then the solutions were filtrated to remove the insoluble parts (<1 wt %). The polymer mixtures in THF were precipitated in methanol (THF/methanol=1/4, v/v), followed by freeze-drying from their benzene solutions overnight to yield yellow viscous products. Polymer mixture yields: 0.64 g, 94% (1 hour) and 0.63 g, 93% (16 hours). $^1$H NMR (CDCl$_3$) for PIB-b-PVFe after fractional precipitation: δ 5.70-5.40 (br, 2H, CH$_2$CH=CHCH$_2$CH), 4.50-3.80 (br, ferrocenyl-H), 2.80-0.80 (br, CH$_2$ and CH).

PIB-AllylBr (M$_n$=15,600, PDI=1.07) was also employed in coupling reactions with PVFeLi (M$_n$=3,600-4,200, PDI=1.08-1.11) in THF at different temperatures, −78° C., −20° C., and 0° C. at the ratio [PVFeLi]/[PIB-AllylBr]=~2. The reaction was sluggish at −78° C. reaching only 8% C.E. (UV) even after 24 h. On the other hand, the C.E. increased to 90% (UV) at −20° C. after 40 h. The coupling reaction readily preceded at 0° C. with 65% (UV) C.E. after only 1 h and with 91% (UV) after 16 h. The results are summarized in Table 2.

Similarly, PIB-AllylCl (M$_n$=15,900, PDI=1.06) and iodoallyl end-functionalized PIB (PIB-AllylI) were reacted with poly(vinylferrocenyl)lithium (PVFeLi, M$_n$=6,220, PDI=1.17) in THF at 0° C. for 16 h. The results are also summarized in Table 2. Additionally, for the coupling of PIB-AllylCl to PVFeLi, there is a large peak for unreacted homo PVFe other than that for the expected AB diblock in RI and UV traces of the coupled product observed by GPC measurement. Since UV source can only detect PVFe segments, the coupling efficiency (C.E.) can simply be determined by the ratio of those two peaks in UV traces taking the feed ratio into consideration. For the coupling of PIB-AllylCl to PVFeLi, the coupling efficiency was only 25%.

Accordingly, the new AB diblock copolymer, PIB-b-PVFe, can be produced by employing PIB-AllylX, and most efficiently with PIB-AllylBr, with relatively high C.E. (>85%) and minor homo PVFe contamination.

Example 3

Coupling reaction of α,ω-Bromoallyl Di-Functionalized PIB (AllylBr-PIB-AllylBr) with Living poly(vinylferrocene)

The precursor, α,ω-chloroallyl di-functionalized PIB (AllylCl-PIB-AllylCl) was first synthesized under a dry nitrogen atmosphere in an MBraun 150-M glove box using Hex/MeCl (60/40, v/v) solvent mixture. The concentrations are as follows; [DicumylCl]=0.001 M, [DTBP]=0.004 M, [IB]=0.625 M, [TiCl$_4$]=0.036 M, and [1,3-butadiene]=0.02 M. IB (312.5 mmol, 17.5 g), initiated by DicumylCl (0.5 mmol) in conjunction with TiCl$_4$ (18 mmol), was polymerized at −80° C. for 1.5 hours in the presence of DTBP (2 mmol) as a proton trap. Then, 1,3-butadiene (10 mmol) was added and allowed to cap at −80° C. for 5 h. After quenching with prechilled methanol (10 mL), the solution was poured in the ammonium hydroxide/methanol (1/9, v/v) mixture. The polymer washed with water/2-propanol/sodium chloride (77.5/15/7.5, v/v/w), precipitated from its hexanes solution into methanol, followed by drying under vacuum to afford AllylCl-PIB-Al-

TABLE 2

Coupling Reaction of PIB-AllylX with PVFeLi in THF$^a$

| | | | homo PVFe | | after coupling reaction | | |
| | | | M$_n$ (g/mol) | | M$_n$ (g/mol)$^b$ | c.e. (%)$^c$ | |
| halogen | temp. (° C.) | time (h) | GPC-MALLS | PDI | high M$_n$/low M$_n$ | UV | $^1$H NMR$^d$ |
|---|---|---|---|---|---|---|---|
| Cl | 0 | 16 | 6,220 | 1.17 | 17,100/6,030 | 25 | 28 |
| Br | −78 | 24 | 3,600 | 1.08 | 17,400/3,800 | 8 | 10 |
| Br | −20 | 40 | 4,350 | 1.09 | 19,900/4,200 | 90 | 81$^e$ |
| Br | 0 | 1 | 4,130 | 1.11 | 19,200/4,030 | 65 | 73 |
| Br | 0 | 16 | 4,130 | 1.11 | 19,600/3,920 | 91 | 85$^e$ |
| I | 0 | 16 | 4,050 | 1.10 | multimodal | 12 | |

$^a$The M$_n$s of PIB-AllylX (X = Cl, Br, and I) are 15,900, 15,600, and 16,000 g/mol, respectively.
$^b$Determined from GPC-MALLS.
$^c$Coupling efficiency.
$^d$Determined by comparing the signal intensities of the methine protons of the unreacted PIB-AllylX and ones at 4.05-3.80 ppm assignable to the cyclopentadienyl protons of the PVFe main chains, assuming no lithium-halogen exchange.
$^e$Determined by the weight ratio of the fractions after isolation of PIB-b-PVFe and homo PVFe with THF/2-butanone mixture.

Figure 4:
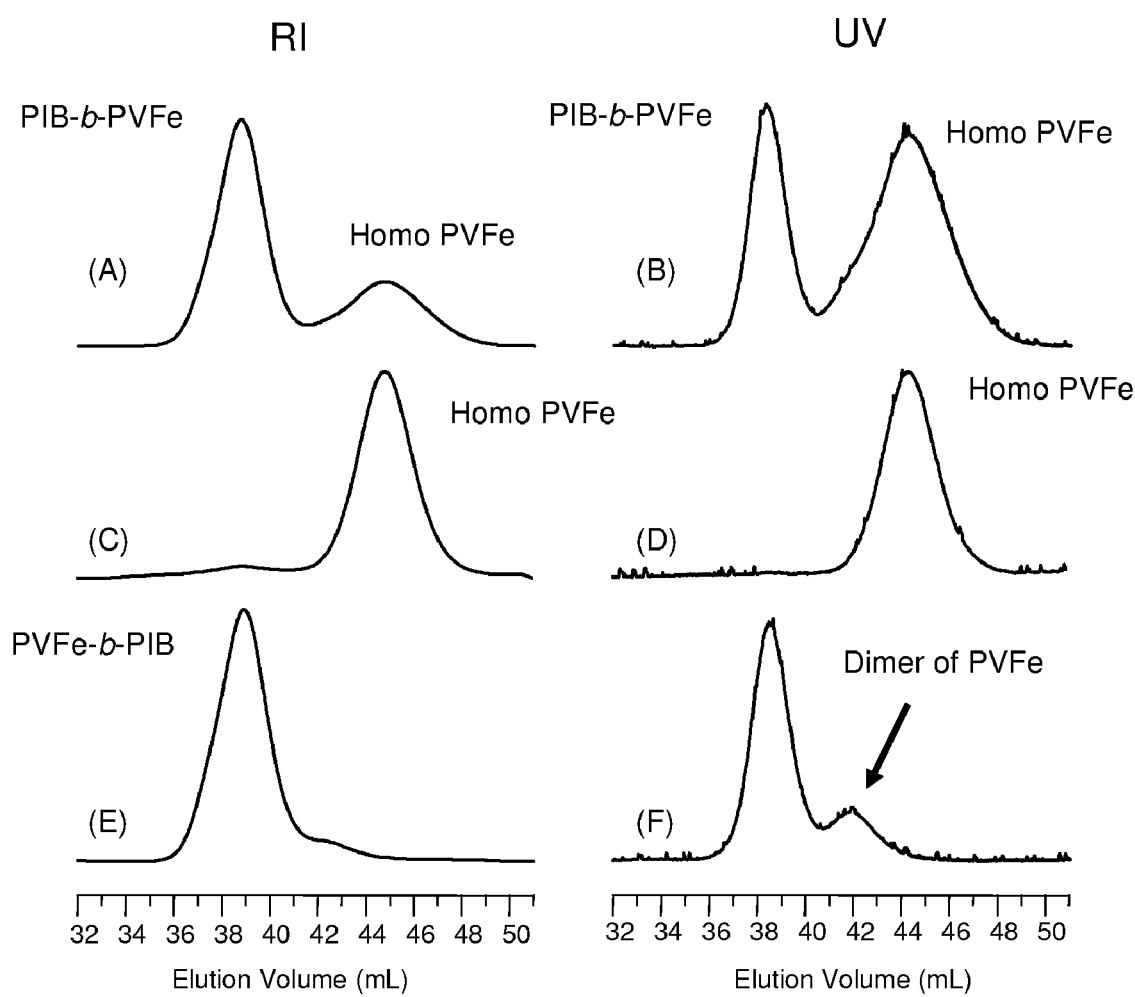
FIGS. 4A-F are graphs depicting GPC RI (A) and UV (B) traces of the product obtained by the coupling reaction of PIB-AllylBr with PVFeLi at 0° C. for 16 h, RI (C) and UV (D) traces for the portion of the reaction mixture soluble in THF/2-butanone, and RI (E) and UV (F) traces for the portion of the reaction mixture insoluble in THF/2-butanone.
Figure 5A:
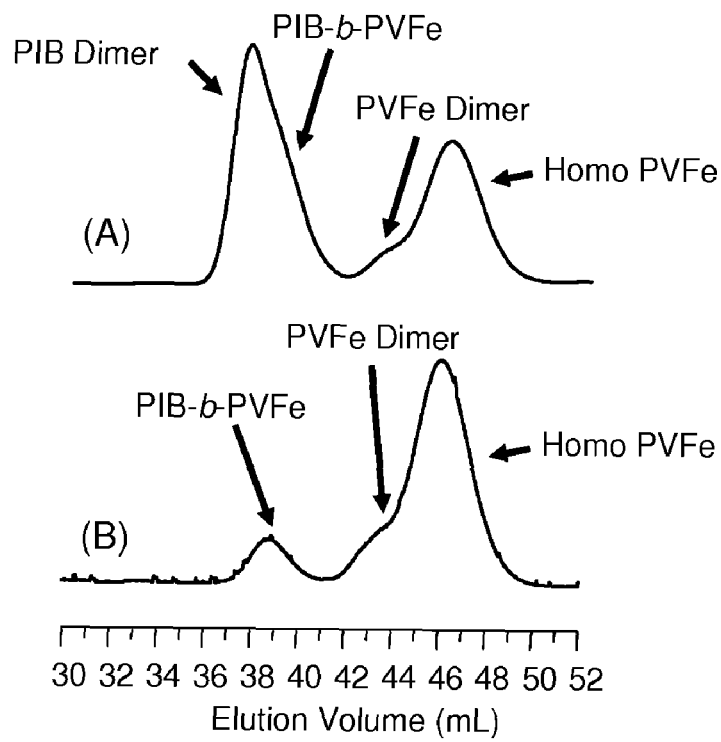
FIG. 5A is a graph depicting GPC RI (A) and UV (B) traces of the product obtained by the coupling reaction of PIB-AllylI with PVFeLi at 0° C. for 16 h.

FIG. 4 shows the GPC RI and UV traces of the product from the coupling of PIB-AllylBr to PVFeLi obtained at 0° C. after 16 h. In these traces there are two peaks corresponding to PIB-b-PVFe (higher M$_n$) and homo PVFe (lower M$_n$) used in excess and unreacted (4(A) and 4(B)). In order to isolate PIB-b-PVFe from the mixture, a THF solution of the product was poured into 2-butanone (THF/2-butanone=1/5, v/v). The C.E. could also be determined by comparing the weight ratio of PIB-b-PVFe and homo PVFe after isolation to give 85%. Unexpectedly, the GPC UV trace of the insoluble part in THF/2-butanone (1/5, v/v) shows a side peak. It is believed that this peak corresponds to the formation of a PVFe dimer (~10 mol %) (4(F)), possibly arising from a lithium-halogen exchange during the coupling reaction resulting in the generation of PVFe bearing a bromine atom at the chain end followed by coupling with PVFeLi. This side reaction is significantly observed when using iodoallyl chain-end functionalized PIB (PIB-AllylI) showing very large PVFe dimer peaks as well as PIB dimer (see FIG. 5A). For this coupling, the yield of PIB-b-PVFe is only 12% after reacting at 0° C. for 16 h.

lylCl. GPC-MALLS: M$_n$=35,100, PDI=1.06, monomodal. $^1$H NMR (CDCl$_3$): δ 7.20 (s, 3H, Ar), 5.85 (p, 2H, C(CH$_3$)$_2$CH$_2$CH=), 5.62 (p, 2H, =CHCH$_2$Cl), 4.05 (d, 4H, CH$_2$Cl), 2.03 (d, 4H, C(CH$_3$)$_2$CH$_2$CH=), 1.89 (s, 4H, ArC(CH$_3$)$_2$CH$_2$), 1.50-1.30 (br, 1237H, CH$_2$), 1.20-0.90 (br, 3732H, CH$_3$). Chloroallyl functionality=2.00.

The polymer (0.142 mmol, 5.0 g) was next treated with anhydrous LiBr (114 mmol) in the toluene/acetone (65/35, v/v) mixture under nitrogen at 80° C. for 24 h. The polymer washed with water three times, and then purified by precipitation in methanol followed by silica gel flash column chromatography using hexanes as an eluent to afford AllylBr-PIB-AllylBr. Finally, the azeotropic distillation from the absolute toluene solution of the polymer was performed three times to remove a trace of water. GPC-MALLS: M$_n$=35,200, PDI=1.07, monomodal. $^1$H NMR (CDCl$_3$): δ7.20 (s, 3H, Ar), 5.85 (p, 2H, C(CH$_3$)$_2$CH$_2$CH=), 5.72 (p, 2H, =CHCH$_2$Br), 3.97 (d, 4H, CH$_2$Br), 2.05 (d, 4H, C(CH$_3$)$_2$CH$_2$CH=), 1.89 (s, 4H, ArC(CH$_3$)$_2$CH$_2$), 1.50-1.30 (br, 1225H, CH$_2$), 1.20-0.90 (br, 3696H, CH$_3$). Bromoallyl functionality=1.98.

Figure 5B:
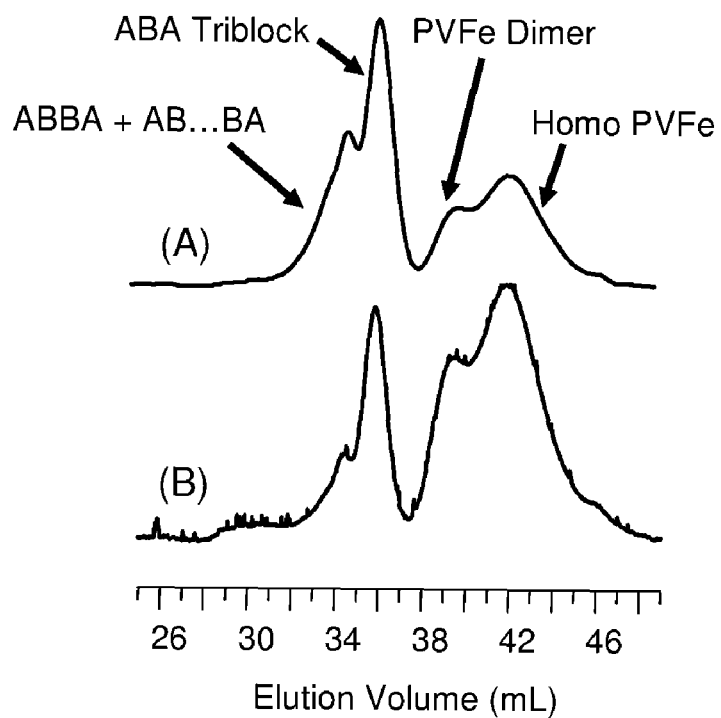
FIG. 5B is a graph depicting GPC RI (A) and UV (B) traces of the product obtained by the coupling reaction of AllylBr-PIB-AllylBr with PVFeLi at 0° C. for 24 h.

To synthesize the ABA triblock copolymer (A=PVFe and B=PIB), the coupling reaction of α,ω-bromoallyl di-functionalized PIB (AllylBr-PIB-AllylBr, $M_n$=35,200, PDI=1.07, bromoallyl functionality=0.99) with a 2.34-fold excess of PVFeLi ($M_n$=9,500, PDI=1.17) toward the bromoallyl functionality was carried out in THF at 0° C. for 24 hours. As shown in FIG. 5B, the GPC trace of the product shows a major peak of the expected ABA triblock copolymer and homo PVFe used in excess accompanied with additional higher molecular weight shoulders. Such shoulders may correspond to ABBA and AB . . . BA multi-blocks as well as the large dimeric PVFe peak. It is believed that these byproducts may arise from the lithium-halogen exchange as described above.

Example 4

Figure 2:
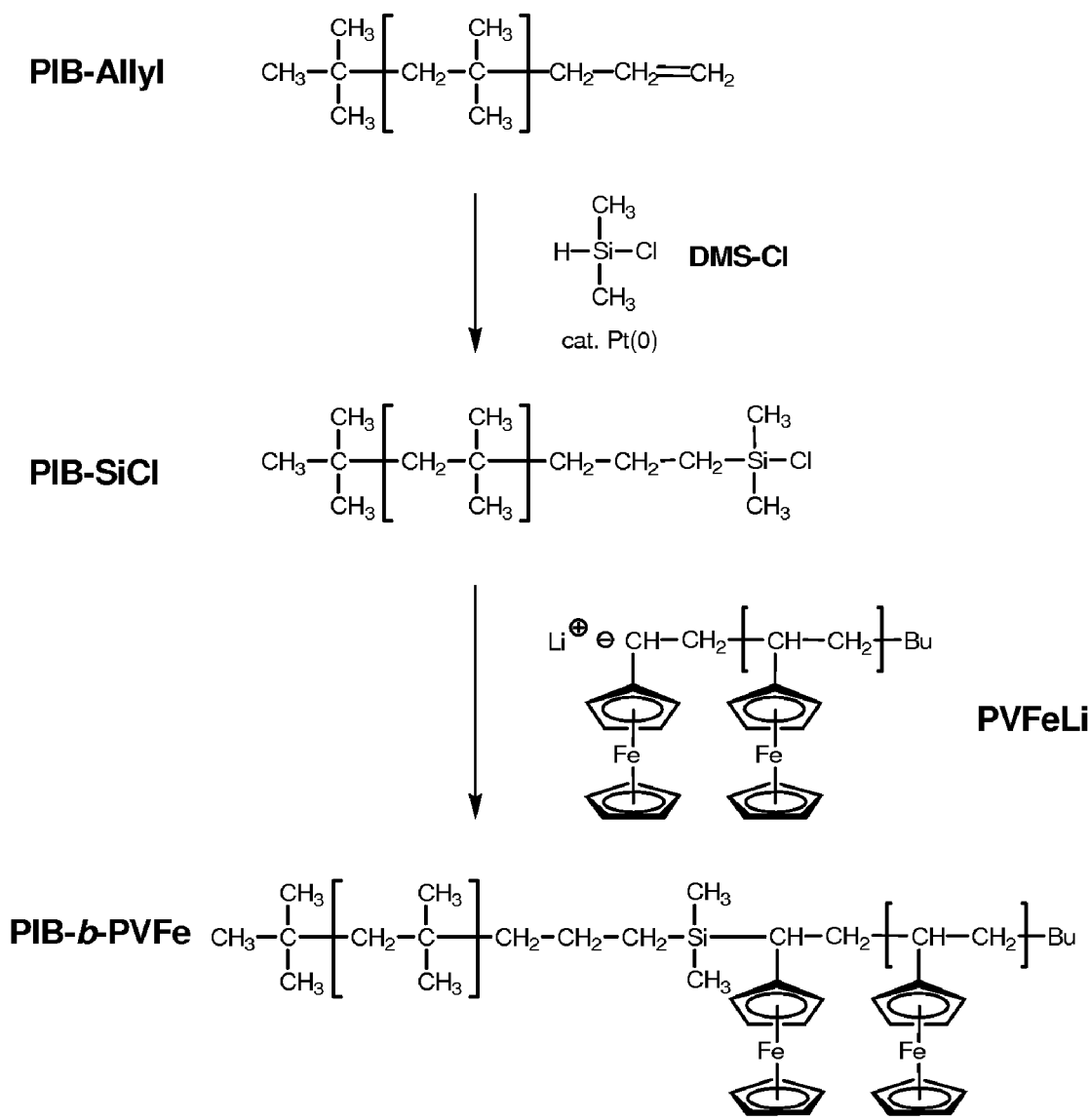
FIG. 2 is a scheme of the synthesis of an exemplary copolymer of the invention, PIB-b-PVFe, by the coupling reaction of PIB-SiCl with PVFeLi.

Hydrosilation of Allyl End-functionalized Polyisobutylene with Chlorodimethylsilane Chlorosilyl chain-end functionalized PIB (PIB-SiCl) was prepared by the hydrosilation reaction between DMS-Cl and an allyl chain-end functionalized PIB (PIB-Allyl) as outlined in FIG. 2. Well dried allyl end-functionalized polyisobutylene (PIB-Allyl, $M_n$=14,200, PDI=1.06, 2.0 g, 0.141 mmol, allyl functionality=1.00) was charged in an apparatus equipped with a condenser, argon inlet, and a break-seal under dry argon and dissolved in dry toluene (30 mL). A 10 mL of toluene was removed by distillation together with a trace of moisture. Chlorodimethylsilane (DMS-Cl, 0.133 g, 1.41 mmol) was subsequently added to the solution followed by injecting a solution of Karstedt's catalyst, $Pt_2[CH_2=CHSi(CH_3)_2OSi(CH_3)_2CH=CH_2]$, in xylene (100 ppm, ca. 10 μL). The solution was stirred at 95° C. for 3 hours under argon. A 5% portion of the solution was taken out for characterization. Toluene was discarded from the rest solution in vacuo and the azeotropic distillation from dry toluene solution was repeated two times. After drying under high vacuum ($10^{-6}$ torr) for 24 hours, chlorosilyl chain-end functionalized PIB (PIB-SiCl) was afforded. The apparatus was sealed off and the polymer was subdivided through the break-seal after dissolving in dry hexanes for the later use. Yield: 1.89 g, 99%. GPC-MALLS: $M_n$=14,200, PDI=1.06, monomodal. $^1$H NMR ($CDCl_3$): δ 3.48 (s, 3H, $OCH_3$), 1.50-1.30 (br, 502H, $CH_2$), 1.20-0.90 (br, 1515H, $CH_3$), 0.60 (t, 2H, —$CH_2Si$), 0.13 (s, 6H, $Si(CH_3)_2$). Chlorosilyl functionality=1.00.

Figure 6A:
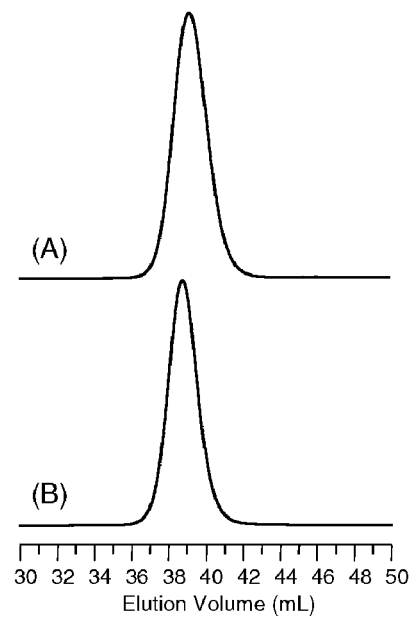
FIG. 6A is a graph depicting GPC RI traces of (A) PIB-Allyl and (B) PIB-SiOMe.
Figure 6B:
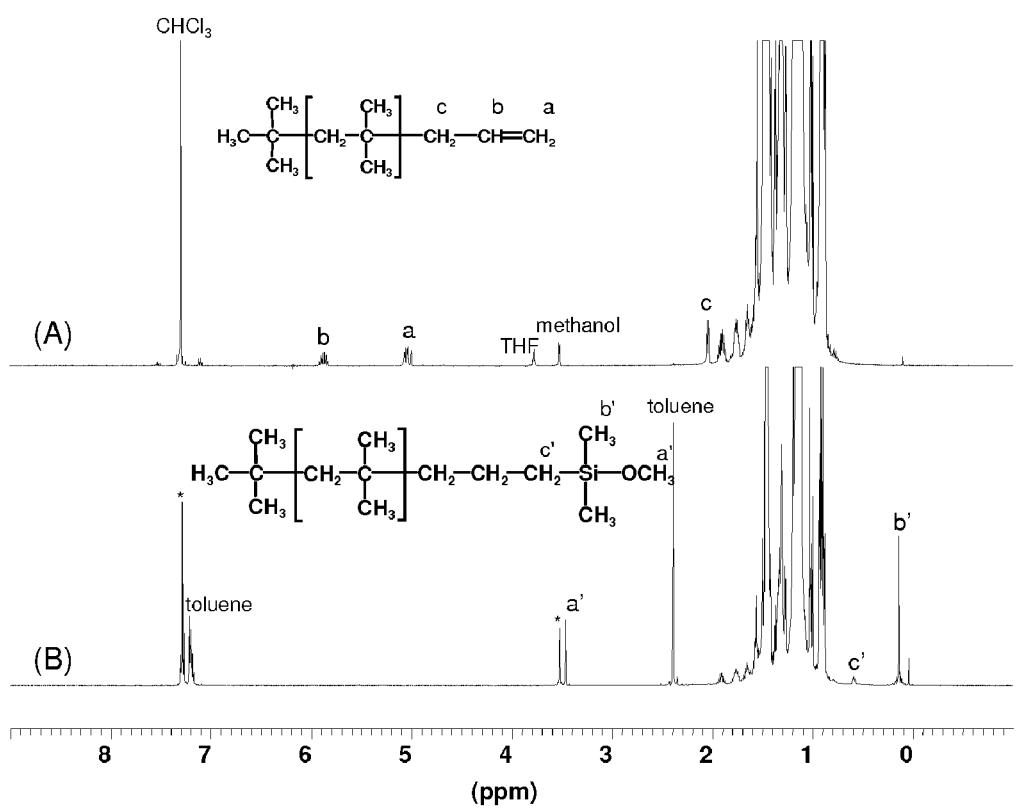
FIG. 6B is a $^1$H NMR spectra of (A) PIB-Allyl and (B) PIB-SiOMe.

The polymers before and after hydrosilation exhibit monomodal GPC RI traces without any big changes in their shape and position (FIG. 6A). In the $^1$H NMR spectrum after hydrosilation (FIG. 6B), characteristic resonances from the two methylene protons (—$CH_2$—CH=), (=$CH_2$), and the one methine proton (—CH=) at 2.05, 5.05, and 5.88 ppm, respectively, of allyl groups completely disappeared, instead distinct resonances from the six methyl protons (—Si($CH_3$)$_2$—), the two methylene protons (—$CH_2$—Si), and three methoxy protons (—$SiOCH_3$) at 0.16, 0.60, and 3.47 ppm, respectively, of dimethylmethoxysilylmethyl groups were clearly observed. Thus, the hydrosilation proceeded quantitatively to afford the expected PIB-SiCl.

Example 5

Synthesis of AB Diblock Copolymer by Coupling of Chlorosilyl End-functionalized Polyisobutylene with Living Poly(Vinylferrocene)

As PIB-SiCl ($M_n$=15,800, PDI=1.07) prepared as in Example 3 contained an excess of DMS-Cl, the azeotropic distillation from its absolute toluene solution twice was performed followed by drying under high vacuum condition (<$10^{-6}$ torr) for 24 hours. The coupling reaction of PIB-SiCl with PVFeLi was then performed in THF at 0° C. under high vacuum in a sealed glass reactor with the ampoules of stock solutions, "BuLi in hexane, VFe in THF, PIB-SiCl in hexanes, and TMS-Cl in hexanes, which was pre-washed with DPH-Li in hexanes. After the washing solution was discarded, "BuLi (0.105 mmol) in hexane was charged in the apparatus. Hexane was completely removed under high vacuum, then a THF stock solution (8.0 mL) of VFe (0.276 g, 1.30 mmol) was added with stirring at 0° C. The solution was allowed to stand at 0° C. for 4 h. After a 20% portion of the solution was taken out by heat-sealing for characterizations, the THF stock solution (5.0 mL) of PIB-SiCl (0.580 g, 0.0408 mmol) was added to the rest solution. After 1 h, the system was quenched with degassed methanol (1.0 mL). The concentrations are as follows; ["BuLi]=0.0131 M and [VFe]=0.163 M for the polymerization, [PVFeLi]=0.00645 M and [PIB-SiCl]=0.00358 M for the coupling reaction. The solution was filtrated to remove the insoluble parts (<1 wt %). The polymer mixtures in THF solution were precipitated in methanol (THF/methanol=1/4, v/v), followed by freeze-drying from their benzene solution overnight to yield a yellow viscous product. Isolation yield of PIB-b-PVFe after fractional precipitation using THF/2-butanone (1/4, v/v): 0.56 g, 80%. GPC-MALLS: $M_n$=16,800, PDI=1.04, monomodal. $^1$H NMR ($CDCl_3$): δ 4.50-3.80 (br, 127H, ferrocenyl-H), 2.80-0.80 (br, 2059H, $CH_2$ and CH), 0.40-0.20 (br, 6H, $CH_2Si(CH_3)_2CH$).

Figure 7:
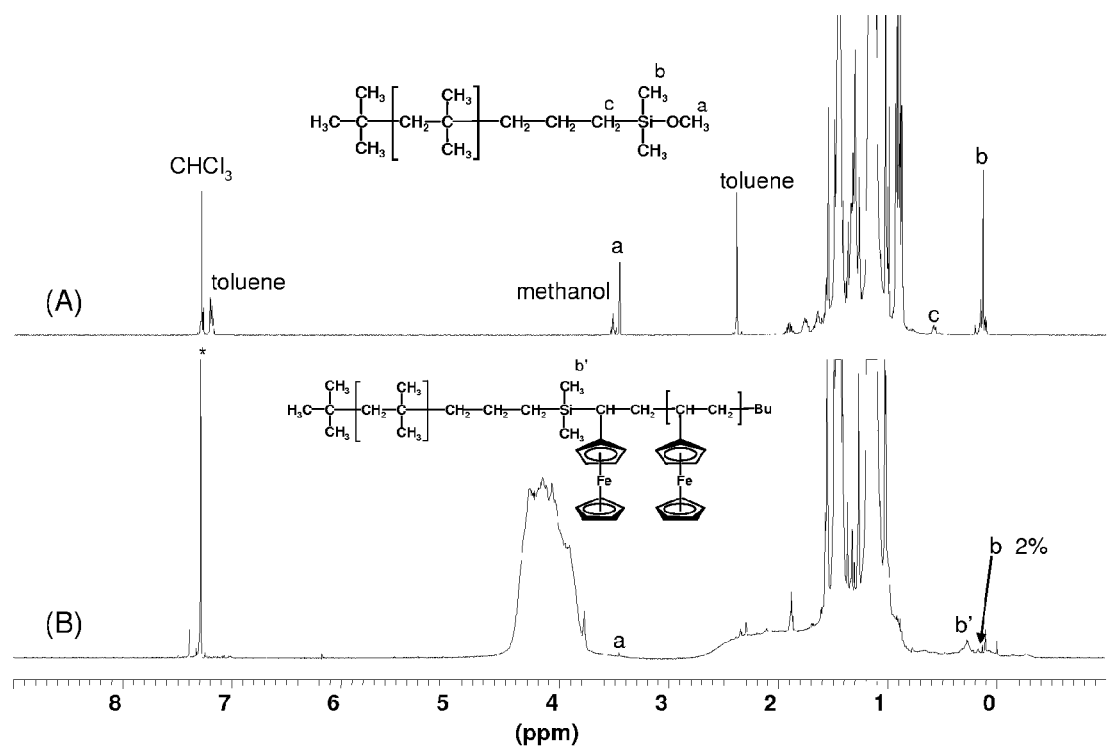
FIGS. 7A-B are $^1$H NMR spectra of (A) PIB-SiOMe and (B) the product obtained by the coupling reaction of PIB-SiCl with PVFeLi at 0° C. at [PVFeLi]/[PIB-SiCl]=2.6.
Figure 8:
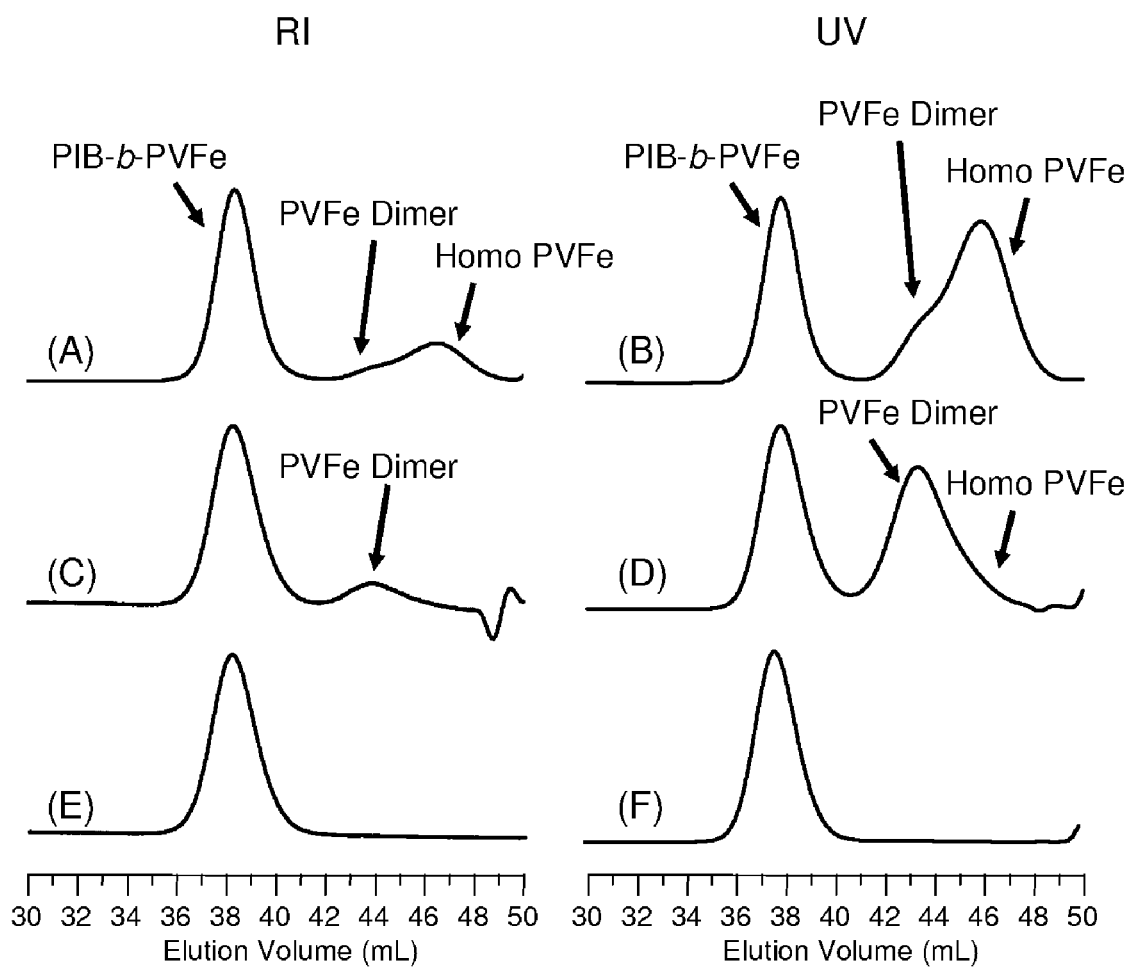
FIGS. 8A-F are graphs depicting GPC RI (A) and UV (B) traces of the product obtained by the coupling reaction of PIB-SiCl with PVFeLi at 0° C. at [PVFeLi]/[PIB-SiCl]=2.6, RI (C) and UV (D) traces at [PVFeLi]/[PIB-SiCl]=1.8, and RI (E) and UV (F) traces for the isolated PIB-b-PVFe ($M_n$=16,800, PDI=1.04).

When ratio of [PVFeLi]/[PIB-SiCl] of 2.6 was utilized, the reaction was much faster than the case with PIB-AllylX, achieving a very high C.E. (UV: 99%) after only 30 minutes. The $^1$H NMR spectrum of the polymer mixture confirmed the efficient coupling reaction showing very small (2%) signal at 0.13 ppm assignable to the silylmethyl protons of PIB-SiOMe which was generated by quenching the unreacted PIB-SiCl with dry methanol. The $^1$H NMR spectrum of the polymer mixture also shows a relatively broad signal at 0.2-0.35 ppm corresponding to the silylmethyl group at the junction between both PIB and PVFe segments (see FIG. 7). By comparing the signals at about 0.13 ppm and 0.2-0.35 ppm, the C.E. was calculated to be 98%. GPC RI and UV traces of the product show three peaks corresponding to PIB-b-PVFe, homo PVFe used in excess, and PVFe dimer, as can be seen in FIGS. 8(A) and (B). It is believed that the dimer may be formed not by the lithium-halogen exchange as in the reactions described in Example 2, but by the coupling between homo PVFeL is used in excess and di-functional low molecular weight byproducts such as dichlorodimethylsilane or dichlorotetramethyldisilane that may possibly be generated during the hydrosilation reaction. Reducing the ratio of [PVFeLi]/[PIB-SiCl] from 2.6 to 1.8 minimized homo PVFe contaminations.

The GPC RI (FIG. 8(C)) and UV (FIG. 8(D)) traces of the product of the reaction having a [PVFeLi]/[PIB-SiCl] ratio of 1.8 show two main peaks of PIB-b-PVFe and PVFe dimer, and very small peak of homo PVFe (detectable in UV) used in excess. The C.E. was still good (95%) and also still close to the value determined from $^1$H NMR (94%). The expected pure PIB-b-PVFe free of homo PVFe as well as its dimer were successfully obtained by the fractional precipitation using THF/2-butanone (1/4, v/v) in an 80% yield, showing a single, sharp, and symmetrical peak in either RI or UV GPC trace (see FIGS. 8(E) and 8(F)). These results are summarized in Table 3.

TABLE 3

Coupling Reaction of PIB—SiCl with PVFeLi in THF at 0° C.

| time (h) | [PVFeLi]/ [PIB—SiCl] | homo PVFe $M_n$ (g/mol) GPC-MALLS | PDI | after coupling reaction $M_n$ (g/mol) | | | c.e. (%)[a] | |
|---|---|---|---|---|---|---|---|---|
| | | | | calcd | GPC-MALLS[b] | PDI | UV | $^1$H NMR[c] |
| 0.5 | 2.6[d] | 2,800 | 1.10 | 18,600 | 18,700 | 1.06 | 99 | 98 |
| 1 | 1.8[e] | 3,000 | 1.10 | 17,200 | 16,800 | 1.04 | 95 | 94 |

[a]Coupling efficiency.
[b]Measured after isolation of PIB-b-PVFe.
[c]Determined by comparing the signal intensities at 0.13 ppm assignable to the silylmethyl protons of PIB—SiOMe and ones at 0.40-0.20 ppm assignable to the silylmethyl protons at the junction between PIB and PVFe segments.
[d]PIB—SiCl ($M_n$ = 15,800, PDI = 1.07) was used.
[e]PIB—SiCl ($M_n$ = 14,200, PDI = 1.06) was used.

PIB-b-PVFes are structurally homogeneous after isolation by the fact that the measured $M_n$ values are in good agreement with those calculated based on the $M_n$ values of PIB-SiCl and PVFe, with very narrow PDIs (<1.06). In addition, the weight compositions PIB/PVFe of the isolated PIB-b-PVFes were determined from $^1$H NMR and agreed with calculated values. Thus, new AB block copolymers (A=PIB and B=PVFe) with very good C.E.s (>94%) and controlled molecular weights, compositions, and narrow PDIs have been synthesized.

Example 6

Hydrosilation of α,ω-allyl Di-functionalized Polyisobutylene with Chlorodimethylsilane Well dried α,ω-allyl di-functionalized polyisobutylene (Allyl-PIB-Allyl, $M_n$=38,500, PDI=1.05, 3.0 g, 0.0777 mmol, allyl functionality=2.00) was charged in an apparatus equipped with a condenser, argon inlet, and a break-seal under dry argon and dissolved in dry toluene (40 mL). A 10 mL of toluene was removed by distillation together with a trace of moisture. Then, DMS-Cl (0.147 g, 1.561 mmol) was added to the solution followed by injecting Karstedt's catalyst, Pt(0), solution in xylene (100 ppm, ca. 10 µL). The solution was stirred at 95° C. for 3 h under argon. A 5% portion of the solution was taken out for characterization. Toluene was discarded from the rest solution in vacuo and the azeotropic distillation from dry toluene solution was repeated two times. After drying under high vacuum ($10^{-6}$ torr) for 24 h, α,ω-chlorosilyl di-functionalized PIB (SiCl-PIB-SiCl) was afforded. The apparatus was sealed off and the polymer was subdivided through the break-seal after dissolving in dry hexanes for the later use. Yield: 3.0 g, 100%. GPC-MALLS: $M_n$=38,600, PDI=1.04, monomodal. $^1$H NMR (CDCl$_3$): δ 7.20 (s, 3H, Ar), 3.48 (s, 3H, OCH$_3$), 1.89 (s, 4H, ArC(CH$_3$)$_2$CH$_2$), 1.50-1.30 (br, 1358H, CH$_2$), 1.20-0.90 (br, 4094H, CH$_3$), 0.60 (t, 2H, —CH$_2$Si), 0.13 (s, 6H, Si(CH$_3$)$_2$). Chlorosilyl functionality=2.00.

Example 7

Synthesis of ABA Triblock Copolymer by Coupling of α,ω-chlorosilyl di-functionalized Polyisobutylene with Living poly(vinylferrocene)

The coupling reaction of SiCl-PIB-SiCl with PVFeLi was performed in THF at 0° C. under high vacuum in a sealed glass reactor with the ampoules of stock solutions, "BuLi in hexane, VFe in THF, SiCl-PIB-SiCl in hexanes, and TMS-Cl in hexanes, which was pre-washed with DPH-Li in hexanes. After the washing solution was discarded, "BuLi (0.118 mmol) in hexane was charged in the apparatus. Hexane was completely removed under high vacuum, then a THF stock solution (10 mL) of VFe (0.997 g, 4.70 mmol) was added with stirring at 0° C. The solution was allowed to stand at 0° C. for 6 h. After a 20% portion of the solution was taken out by heat-sealing for characterizations, the THF stock solution (5.0 mL) of SiCl-PIB-SiCl (0.380 g, 0.0982 mmol) was added to the rest solution. After 4 h, the system was quenched with degassed methanol (1.0 mL). The concentrations are as follows; ["BuLi]=0.0118 M and [VFe]=0.47 M for the polymerization, [PVFeLi]=0.00236 M and [SiCl-PIB-SiCl]= 0.000655 M for the coupling reaction. The solution was filtrated to remove the insoluble parts (<1 wt %). The polymer mixtures in THF solution were precipitated in methanol (THF/methanol=1/4, v/v), followed by freeze-drying from their benzene solution overnight to yield a yellow viscous product. Isolation yield of PVFe-b-PIB-b-PVFe after fractional precipitation using THF/2-butanone (1/1, v/v): 0.40 g, 73%. GPC-MALLS: $M_n$=56,600, PDI=1.08, monomodal. $^1$H NMR (CDCl$_3$): δ 7.20 (s, 3H, Ar), 4.50-3.80 (br, 849H, ferrocenyl-H), 2.80-0.80 (br, 5735H, CH$_3$), 0.40-0.20 (br, 6H, CH$_2$Si(CH$_3$)$_2$CH).

Figure 9:
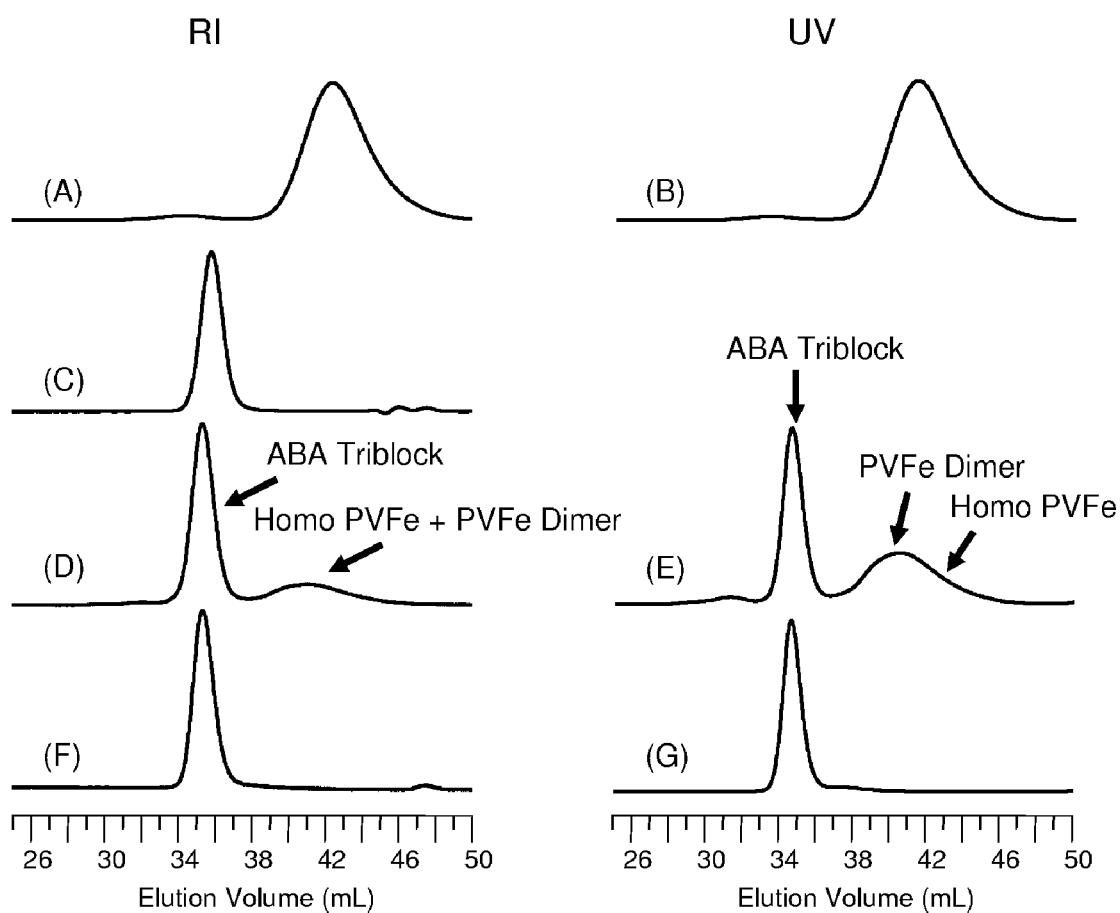
FIGS. 9A-G are graphs depicting GPC RI and UV traces of homo PVFe (RI: (A) and UV: (B)), the product after treating SiCl-PIB-SiCl with methanol (RI: (C)), the product obtained by the coupling reaction (RI: (D) and UV: (E)), and the isolated PVFe-b-PIB-b-PVFe (RI: (F) and UV: (G)).
Figure 10:
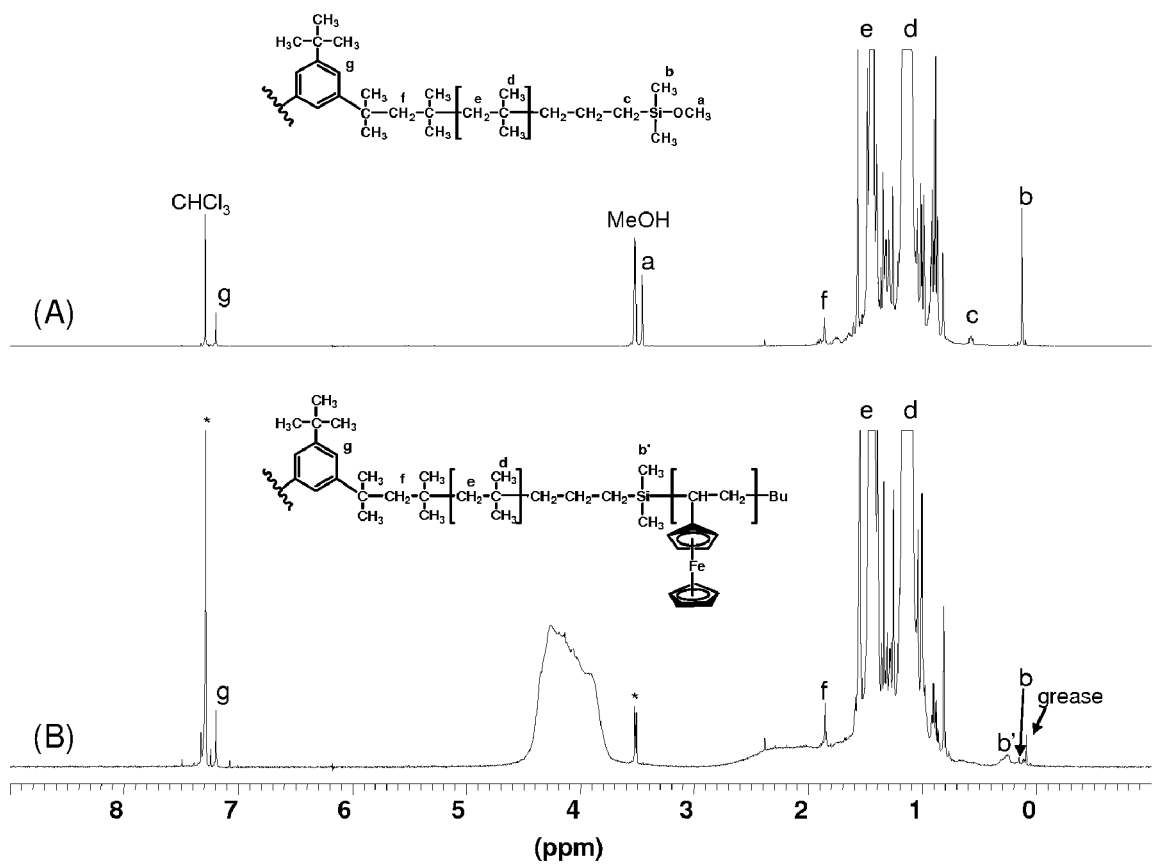
FIGS. 10A-B are $^1$H NMR spectra of (A) the product after treating SiCl-PIB-SiCl with dry methanol and (B) the product obtained by the coupling reaction of SiCl-PIB-SiCl with PVFeLi.

As shown in FIGS. 9(D) and 9(E), the GPC RI and UV traces of the product show two peaks corresponding to the expected ABA triblock and the mixture of homo PVFe and its dimer. By comparing two peak areas in UV trace, the C.E. was 98%. The C.E. was confirmed by $^1$H NMR (99.2%) displaying almost negligible amount (0.8%) of the signal at 0.13 ppm assignable to the silylmethyl protons of the SiOMe group (see FIG. 10). The expected PVFe-b-PIB-b-PVFe could be isolated by the fractional precipitation using THF/ 2-butanone (1/1, v/v) in a 73% yield. Either RI or UV GPC trace (see FIGS. 9(F) and 9(G)) shows a monomodal, sharp, and symmetrical peak, indicating that the polymer is free of homo PVFe contamination.

The $M_n$ value of the isolated PVFe-b-PIB-b-PVFe is 56,600 g/mol, which agrees with the calculated value of 55,600 g/mol, and PDI is very narrow at 1.08. Furthermore, the weight composition PIB/PVFe was 70/30 determined from $^1$H NMR close to the calculated 69/31. Thus, the well-defined ABA triblock copolymer of PVFe-b-PIB-b-PVFe was synthesized with a C.E of >98%.

What is claimed is:
1. A copolymer comprising (a) at least one polymer block comprising a plurality of constitutional units that correspond to at least one cationically polymerizable isomonoolefin species and (b) at least one polymer block comprising a plurality of constitutional units that correspond to at least one anionically polymerizable monomer species selected from the group consisting of monomers of formula (I):

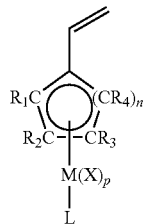

wherein
R$_1$, R$_2$, R$_3$ and each occurance of R$_4$ are each independently selected from the group consisting of hydrogen, C$_1$-C$_{20}$ alkyl, C$_1$-C$_{20}$ alkyl substituted with C$_1$-C$_{20}$ aryl, C$_1$-C$_{20}$ aryl, halogen, C$_1$-C$_{20}$ haloalkyl, hydroxyl, C$_1$-C$_{20}$ alkoxy, amino, C$_1$-C$_{20}$ alkylamino, di(C$_1$-C$_{20}$ alkyl)amino, thiol, C$_1$-C$_{20}$ alkylthio, carboxylate, C$_1$-C$_{20}$ acyl, nitro, cyano, or at least two R groups are taken together to form a fused ring structure;
n is an integer of 1 or 2;
p is an integer of 0 or 1;
M is a metal;
X is a counterion; and
L is one or more ancillary ligands; and
(c) at least one functional group selected from allyl and silyl, wherein the functional group is located between at least one cationically polymerizable isomonoolefin species and at least one anionically polymerizable monomer species.

2. The copolymer of claim 1, wherein n is 1.

3. The copolymer of claim 1, wherein L is a ligand of formula (II):

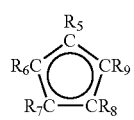

wherein R$_5$, R$_6$, R$_7$, R$_8$ and R$_9$ are each independently selected from the group consisting of hydrogen, C$_1$-C$_{20}$ alkyl, C$_1$-C$_{20}$ alkyl substituted with C$_1$-C$_{20}$ aryl, C$_1$-C$_{20}$ aryl, halogen, C$_1$-C$_{20}$ haloalkyl, hydroxyl, C$_1$-C$_{20}$ alkoxy, amino, C$_1$-C$_{20}$ alkylamino, di(C$_1$-C$_{20}$ alkyl)amino, thiol, C$_1$-C$_{20}$ alkylthio, carboxylate, C$_1$-C$_{20}$ acyl, nitro, cyano, or at least two R groups are taken together to form a fused ring structure.

4. The copolymer of claim 1, wherein M is a metal selected from the group consisting of Fe, Co, Ni, Ru, Ti, Zr or Os.

5. The copolymer of claim 1, wherein the monomer of formula (I) is at least one monomer selected from the group consisting of vinylferrocene, vinylcobaltocene, vinylnickelocene, vinylruthenocene, vinyltitanocene, vinylzirconocene, and vinylosmocene.

6. The copolymer of claim 1, wherein the cationically polymerizable isomonoolefin species is at least one isomonoolefin species selected from the group consisting of isobutylene, 2-methylbutene, 3-methyl-1-butene, 4-methyl-1-pentene and beta-pinene.

7. The copolymer of claim 1, wherein the number average molecular weight of the copolymer ranges from about 10,000 to about 1,000,000.

8. The copolymer of claim 1, wherein the plurality of constitutional units that correspond to at least one cationically polymerizable isomonoolefin species comprises a plurality of constitutional units that correspond to a single cationically polymerizable isomonoolefin species.

9. The copolymer of claim 1, wherein the cationically polymerizable isomonoolefin species comprises isobutylene.

10. The copolymer of claim 1, wherein the plurality of constitutional units that correspond to at least one anionically polymerizable monomer species comprises a plurality of constitutional units that correspond to a single anionically polymerizable monomer species.

11. The copolymer of claim 1, wherein the anionically polymerizable monomer species comprises vinylferrocene.

12. The copolymer of claim 1, wherein said copolymer is a linear copolymer.

13. The copolymer of claim 1, wherein said copolymer is a branched copolymer.

14. A method for making a copolymer comprising:
contacting an end functionalized polyisomonoolefin with a living organometallic polymer in the presence of an initiator, wherein the living organometallic polymer comprises a plurality of constitutional units that correspond to at least one anionically polymerizable monomer species selected from the group consisting of monomers of formula (I):

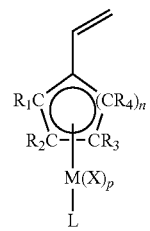

wherein
R$_1$, R$_2$, R$_3$ and each occurance of R$_4$ are each independently selected from the group consisting of hydrogen, C$_1$-C$_{20}$ alkyl, C$_1$-C$_{20}$ alkyl substituted with C$_1$-C$_{20}$ aryl, C$_1$-C$_{20}$ aryl, halogen, C$_1$-C$_{20}$ haloalkyl, hydroxyl, C$_1$-C$_{20}$ alkoxy, amino, C$_1$-C$_{20}$ alkylamino, di(C$_1$-C$_{20}$ alkyl)amino, thiol, C$_1$-C$_{20}$ alkylthio, c arboxyl ate , C$_1$-C$_{20}$ acyl, nitro, cyano, or at least two R groups are taken together to form a fused ring structure;
n is an integer of 1 or 2;
p is an integer of 0 or 1;
M is a metal;
X is a counterion; and
L is one or more ancillary ligands;
wherein the end functionalized polyisomonoolefin is an allyl-halide end functionalized polyisomonoolefin or a silyl end functionalized polyisomonoolefin.

15. The method of claim 14, wherein the monomer of formula (I) is at least one monomer selected from the group consisting of vinylferrocene, vinylcobaltocene, vinylnickelocene, vinylruthenocene, vinyltitanocene, vinylzirconocene, and vinylosmocene.

16. The method of claim 14, wherein the end functionalized polyisomonoolefin is an allyl-halide end functionalized polyisomonoolefin.

17. The method of claim 14, wherein the end functionalized polyisomonoolefin is a silyl end functionalized polyisomonoolefin.

18. The method of claim 14, wherein the polyisomonoolefin is polyisobutylene.

19. The method of claim 14, wherein the initiator is at least one initiator selected from the group consisting of methyllithium, ethyllithium, isopropyllithium, n-butyllithium, sec-butyllithium, tert-butyllithium, tert-octyllithium, phenyllithium, 1-naphthyllithium, p-tolyllithium, cyclohexyllithium and 4-cyclohexylbutyllithium.

20. An article of manufacture comprising at least one copolymer of claim 1.

21. The article of manufacture of claim 20, wherein the article of manufacture is an insertable or implantable medical device.

22. The article of manufacture of claim 21, wherein the implantable medical device is a device selected from the group consisting of a catheter, an endotracheal tube, a tracheostomy tube, a wound drainage device, a wound dressing, a stent, an implant, an intravenous catheter, a medical adhesive, a suture, a shunt, a gastrostomy tube, medical tubing, a cardiovascular product, a heart valve, a pacemaker lead, a guidewire and a urine collection device.

* * * * *